(12) United States Patent
Castro-Palomino Laria et al.

(10) Patent No.: US 10,253,017 B2
(45) Date of Patent: Apr. 9, 2019

(54) DERIVATIVES OF 2-AMINOPYRIDINE AS ADENOSINE $A_{2B}$ RECEPTOR ANTAGONISTS AND LIGANDS OF THE MELATONIN $MT_3$ RECEPTORS

(71) Applicant: PALOBIOFARMA, S.L., Mataró, Barcelona (ES)

(72) Inventors: Julio Cesar Castro-Palomino Laria, Barcelona (ES); Juan Alberto Camacho Gómez, Barcelona (ES); Adela Mendoza Lizaldez, Barcelona (ES)

(73) Assignee: PALOBIOFARMA, S.L., Mataró, Barcelona (ES)

( * ) Notice: Subject to any disclaimer, the term of this patent is extended or adjusted under 35 U.S.C. 154(b) by 0 days.

(21) Appl. No.: 15/552,039

(22) PCT Filed: Feb. 19, 2016

(86) PCT No.: PCT/EP2016/053509
§ 371 (c)(1),
(2) Date: Aug. 18, 2017

(87) PCT Pub. No.: WO2016/135048
PCT Pub. Date: Sep. 1, 2016

(65) Prior Publication Data
US 2018/0037569 A1     Feb. 8, 2018

(30) Foreign Application Priority Data

Feb. 25, 2015 (ES) .................................. 201530233

(51) Int. Cl.
| C07D 401/14 | (2006.01) |
| A61K 45/06 | (2006.01) |
| A61K 31/506 | (2006.01) |
| A61K 31/444 | (2006.01) |

(52) U.S. Cl.
CPC .......... *C07D 401/14* (2013.01); *A61K 31/444* (2013.01); *A61K 31/506* (2013.01); *A61K 45/06* (2013.01)

(58) Field of Classification Search
CPC .... C07D 401/14; A61K 45/06; A61K 31/506; A61K 31/444
See application file for complete search history.

(56) References Cited

U.S. PATENT DOCUMENTS

| 6,465,660 B1 | 10/2002 | Wierzbicki et al. |
| 6,750,232 B2 | 6/2004 | Harada et al. |
| 7,317,017 B2 | 1/2008 | Kalla et al. |
| 7,855,202 B2 | 12/2010 | Vidal Juan et al. |
| 8,143,249 B2 | 3/2012 | Kalla et al. |
| 8,466,129 B2 | 6/2013 | Zeng et al. |
| 2002/0173531 A1 | 11/2002 | Wierzbicki et al. |
| 2004/0204449 A1 | 10/2004 | Poissonnier-Durieux et al. |
| 2009/0023763 A1 | 1/2009 | Vidal Juan et al. |
| 2009/0233938 A1 | 9/2009 | Press et al. |

FOREIGN PATENT DOCUMENTS

| EP | 1466604 A1 | 10/2004 |
| EP | 1308441 B1 | 10/2009 |
| FR | 2821843 A1 | 9/2002 |
| FR | 2822153 A1 | 9/2002 |
| WO | 2004106337 A1 | 12/2004 |
| WO | 2005012282 A1 | 2/2005 |
| WO | 2005070926 A1 | 8/2005 |
| WO | 2005100353 A1 | 10/2005 |
| WO | 2006044610 A1 | 4/2006 |
| WO | 2006138376 A1 | 12/2006 |
| WO | 2007039297 A1 | 4/2007 |

OTHER PUBLICATIONS

Sorrentino et al., J. Cancer Metastasis Treat, 2017, 3:127-138.*
Marzagalli et al., Neural Regen Res 2015, 10(2), 205-207.*
Sachdeva et al., Saudi Pharmaceutical Journal 2013, 21, 245-253.*
Baraldi et al., Purinergic Signalling (2008), 4, 287-303.*
Pardo et al., Molecular Aspects of Medicine, 55, 2017, 90-101.*
Polosa et al., Trends in Pharmacological Sciences, 2009, vol. 30, No. 10, 528-535.*
RN-1214323-49-5, 2010, caplus registry.*
RN-1214363-54-8, 2010, caplus registry.*
Thompson et al., 2005, caplus an 2005:179880.*
Erlich, SS et al, The pineal gland: anatomy, physiology, and clinical significance, J Neurosurg, 1985, vol. 63, pp. 321-341.
OBrien, I. A. D. et al. Abnormal circadian rhythm of melatonin in diabetic autonomic neuropathy. Clinical Endocrinology, 1986, vol. 24, pp. 359-364; Abstract Only.
Duncan MJ, et al, (1988). 2-[125I] iodomelatonin binding sites in hamster brain membranes: pharmacological characteristics and regional distribution. Endocrinology, 1988, vol. 122, pp. 1825-1833.

(Continued)

*Primary Examiner* — Sun Jae Yoo
(74) *Attorney, Agent, or Firm* — Tristan A. Fuierer; Olive Law Group, PLLC

(57) ABSTRACT

The present invention relates to novel pyridine derivatives of formula (I):

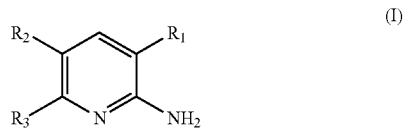

as $A_{2B}$ adenosine receptor antagonists and ligands of $MT_3$ melatonin receptor, to processes for their preparation, to pharmaceutical compositions comprising said compounds and to the use of said for manufacturing a medicament for the treatment of pathological conditions or diseases that can improve by antagonizing the adenosine $A_{2B}$ receptor and by inhibition of $MT_3$ melatonin receptor, such as respiratory disease, metabolic disorders, neurological disorders and cancer.

14 Claims, No Drawings

(56) References Cited

OTHER PUBLICATIONS

Melatonin-Clinical Perspectives, Book Review, J. Psychopharmacology, 3(2), 1989, pp. 121-122.

Lewis AJ, et al, Neuropharmacology of pineal secretions, Drug Metabol Drug Interact. 1990; vol. 8, pp. 247-312; Abstract Only.

Pickering, D.S et al. Pharmacological characterization of melatonin binding sites in Syrian hamster hypothalamus, Eur J. Pharmacol, 1990, vol. 175, pp. 71-77.

Skene, DJ et al, Daily variation in the concentration of melatonin and 5-methoxytryptophol in the human pineal gland: effect of age and Alzheimer's disease, Brain Research, 1990, vol. 528, pp. 170-174.

Giaid, et al, Expression of endothelin-1 in the lungs of patients with pulmonary hypertension, N. Engl. J. Med, 1993, vol. 329, 1732-1739.

Ingemar Bylesj E. et al. Obesity treated with phototherapy: four case studies. International Journal of Eating Disorders, 1996, vol. 20, pp. 443-446.

Feoktistov I, et al, Adenosine A2B receptors as therapeutic targets, Drug Dev Res, 1998, vol. 45, pp. 198-206.

Landells LJ, et al, The role of adenosine receptors in the action of theophylline on human peripheral blood mononuclear cells from healthy and asthmatic subjects, Br. J. Pharmacol, 2000, vol. 129, pp. 1140-1144.

Nosjean, O et al, Identification of the melatonin-binding site MT3 as the quinone reductase 2, J Biol Chem, 2000, vol. 275, 31311-31317.

Fredholm et al., International Union of Pharmacology. XXV. Nomenclature and classification of adenosine receptors, Pharmacol Rev., 2001, vol. 53, pp. 527-552.

Rosi S et al, The influence of brain inflammation upon neuronal adenosine A2B receptors, J Neurochem, 2003, vol. 86, pp. 220-227.

Cronstein, BC, 2011, Adenosine receptors and fibrosis: a translational review, F1000 Biology Reports, 2011, vol. 3: 21 doi: 10.3410/B3-21.

Volpini R, et al, Medicinal chemistry and pharmacology of A2B adenosine receptors, Curr Top Med Chem, 2003, vol. 3, pp. 427-443.

Cicala, C., et al. "Adenosine signaling in airways:Toward a promising antiasthmatic approach," Eur J Pharmacol, 2013, vol. 714, pp. 522-525.

Chunn JL et al, Partially adenosine deaminase-deficient mice develop pulmonary fibrosis in association with adenosine elevations, Am J Physiol Lung Cell Mol Physiol, 2006, vol. 290, L579-L587.

Rüsing, D et al, The impact of adenosine and A2B receptors on glucose homeostasis, J Pharm Pharmacol. 2006, vol. 58, pp. 1639-1645.

Sun CX, et al, Role of A2B adenosine receptor signaling in adenosine-dependent pulmonary inflammation and injury, J Clin Invest, 2006 vol. 116, pp. 2173-2182.

Varani K et al, Alteration of adenosine receptors in patients with chronic obstructive pulmonary disease. Am J Respir Crit Care Med, 2006, vol. 173, pp. 398-406.

Mustafa SJ, et al, Effect of a specific and selective A2B adenosine receptor antagonist on adenosine agonist AMP and allergen-induced airway responsiveness and cellular influx in a mouse model of asthma, J Pharmacol Exp Ther, 2007, vol. 320, pp. 1246-1251.

Selman M et al, Accelerated Variant of Idiopathic Pulmonary Fibrosis: Clinical Behavior and Gene Expression Pattern, 2007, PLoS One, 2(5), e482; doi:10.1371/journal.pone.0000482.

Boutin JA et al, Studies of the melatonin binding site location onto quinone reductase 2 by directed mutagenesis, Arch Biochem Biophys, 2008, vol. 477, pp. 12-19.

Fu, Y et al, Quinone Reductase 2 Is a Catechol Quinone Reductase, Biol Chem, 2008, vol. 283, pp. 23829-23835.

Fishman P. et al, Adenosine Receptors and Cancer, Handb Exp Pharmacol, 2009, vol. 193, 399-441.

Simonneau et al, Updated clinical classification of pulmonary hypertension, 2013, J Am Coll Cardio, vol. 62, No. 25, Suppl. D, pp. D34-D41.

Steiner, et al., Interleukin-6 overexpression induces pulmonary hypertension, 2009, Circ. Res., vol. 104, pp. 236-244.

Benoit CE et al, Loss of quinone reductase 2 function selectively facilitates learning behaviours, 2010, The Journal of Neuroscience, 2010, vol. 30, 12690-12700.

Edwin SL et al, Adenosine in fibrosis, Mod Rheumatol, 2010, vol. 20, pp. 114-122.

Zhou Y, et al, Alterations in Adenosine Metabolism and Signaling in Patients with Chronic Obstructive Pulmonary Disease and Idiopathic Pulmonary Fibrosis, 2010, PLoS One, vol. 5, e9224. doi:10.1371/journal.pone.0009224.

Hashimoto, T et al, Increased hippocampal quinone reductase 2 in Alzheimer's disease, Neurosci Lett, 2011, vol. 502, pp. 10-12.

Akgedik, R et al, Effect of Resveratrol on Treatment of Bleomycin-Induced Pulmonary Fibrosis in Rats, Inflammation, 2012, vol. 35, pp. 1732-1741.

Johnston-Cox H, et al, The A2B Adenosine Receptor Modulates Glucose Homeostasis and Obesity, 2012, PLoS One vol. 7, e40584, doi: 10.1371/journal.pone.0040584.

Karmouty-Quintana, H et al, The A2B adenosine receptor modulates pulmonary hypertension associated with interstitial lung disease, 2012, FASEB J., vol. 26, pp. 2546-2557.

Popoli, P, Pepponi, R, Potential Therapeutic Relevance of Adenosine A2B and A2A Receptors in the Central Nervous System, CNS & Neurological Disorders—Drug Targets, 2012, vol. 11, pp. 664-674.

Caruso M, et al. Adenosine signaling pathways as potential therapeutic targets in respiratory disease, Expert Opin. Ther. Targets, 2013, vol. 17, pp. 761-772.

Desmet C J et al, Identification of a pharmacologically tractable Fra-1/ ADORA2B axis promoting breast cancer metastasis, PNAS, 2013, vol. 110, pp. 5139-5144.

Iannone, R et al, Blockade of A2b Adenosine Receptor Reduces Tumor Growth and Immune Suppression Mediated by Myeloid-Derived Suppressor Cells in a Mouse Model of Melanoma 1,2, Neoplasia, 2013, vol. 15, pp. 1400-1409.

Karmouty-Quintana H, et al., ADORA2B and Hyaluronan modulate Pulmonary Hypertension associated with Chronic Obstructive Pulmonary Disease, AJRCMB Articles in Press, 2013, 10.1165/rcmb.2013-0089OC.

St John SE et al, Design, synthesis, biological and structural evaluation of functionalized resveratrol analogues as inhibitors of quinone reductase 2, Bioorg Med Chem, 2013, vol. 21, pp. 6022-6037.

Wei Q et al, A2B adenosine receptor blockade inhibits growth of prostate cancer cells, Purinergic Signalling, 2013, vol. 9, pp. 271-280.

Pejman, L, et al. The effect of adenosine A2A and A2B antagonists on tracheal responsiveness, serum levels of cytokines and lung inflammation in guinea pig model of asthma, Advanced Pharmaceutical Bulletin, 2014, vol. 4, pp. 131-138.

Handbook of Experimental Pharmacology, Adenosine Receptors in Health and Disease, 2009, vol. 193, pp. 239-362.

International Search Report, dated Jun. 22, 2016.

World Health Organization, "What are neurological disorders?" 2018, http://www.who.int/features/qa/55/en/.

* cited by examiner

DERIVATIVES OF 2-AMINOPYRIDINE AS ADENOSINE $A_{2B}$ RECEPTOR ANTAGONISTS AND LIGANDS OF THE MELATONIN $MT_3$ RECEPTORS

CROSS-REFERENCE TO RELATED APPLICATIONS

This application is filed under the provisions of 35 U.S.C. § 371 and claims the priority of International Patent Application No. PCT/EP2016/053509 filed on 19 Feb. 2016 entitled "DERIVATIVES OF 2-AMINOPYRIDINE AS ADENOSINE $A_{2B}$ RECEPTOR ANTAGONISTS AND LIGANDS OF THE MELATONIN $MT_3$ RECEPTORS" in the name of Julio CASTRO-PALOMINO LARIA, et al., which claims priority to Spanish Patent Application No. P201530233, filed on 25 Feb. 2015, both of which are hereby incorporated by reference herein in their entirety.

FIELD OF THE INVENTION

The present invention relates to novel pyridine derivatives as $A_{2B}$ adenosine receptor antagonists and ligands of $MT_3$ melatonin receptor.

Other objectives of the present invention are to provide a process for the preparation of said compounds; pharmaceutical compositions comprising an effective amount of said compounds; the use of said compounds for manufacturing a medicament for the treatment of pathological conditions or diseases susceptible of improvement by antagonizing the adenosine $A_{2B}$ receptor and by inhibition of the $MT_3$ melatonin receptor, such as respiratory diseases, metabolic disorders, neurological disorders and cancer

STATE OF THE ART

Adenosine regulates its function through four subtypes of receptors which are $A_1$, $A_{2A}$, $A_{2B}$ and $A_3$. These receptors are grouped according to effects on adenilate cyclase. The $A_1$ and $A_3$ receptors inhibit the production of cAMP through coupling to protein G. The $A_{2A}$ and $A_{2B}$ receptors increase the levels of cAMP by stimulating of the enzyme adenylate cyclase and by coupling to protein G, as well.

Related with the affinity of all the receptors subtypes to its natural ligand adenosine, it is known that the $A_{2B}$ receptor has the lowest affinity, $A_3$ receptor has intermediate affinity and $A_1$ and $A_{2A}$ receptors have the highest affinity. In this sense, it has been suggested that the adenosine $A_{2B}$ receptor is silent under physiological conditions, and is activated in situations of increased extracellular adenosine levels, such as hypoxia.

Potential of Adenosine $A_{2B}$ Receptor Modulators in the Treatment of Respiratory Diseases Several scientific publications have shown the potential of $A_{2B}$ receptors antagonists for the treatment of respiratory diseases and inflammation (Feoktistov I, et al, *Adenosine $A_{2B}$ receptors as therapeutic targets*. Drug Dev Res 45: 198-206, 1998; Rosi S et al, *The influence of brain inflammation upon neuronal adenosine $A_{2B}$ receptors*. J Neurochem 86: 220-227, 2003; Mustafa S J, et al, *Effect of a specific and selective $A_{2B}$ adenosine receptor antagonist on adenosine agonist AMP and allergen-induced airway responsiveness and cellular influx in a mouse model of asthma*. J Pharmacol Exp Ther 320: 1246-1251, 2007; Sun CX, et al, *Role of $A_{2B}$ adenosine receptor signaling in adenosine-dependent pulmonary inflammation and injury*. J Clin Invest 116: 2173-2182, 2006).

Adenosine can impact both degranulation of mast cells and the production of inflammatory mediators. Recently, emerging evidences suggest that $A_{2B}$ adenosine receptors mediate the production and release of pro-inflammatory mediators as IL-8, IL-4 and IL-3 from mast cells. For this reason, it is considered that $A_{2B}$ antagonists receptors might be promising therapeutic agents in the treatment of asthma, chronic obstructive pulmonary disease (COPD), pulmonary hypertension (PH) and pulmonary fibrosis.

a) Asthma

Asthma is a lung disease characterized by airways hyper-responsiveness and inflammation. The physiological effects of adenosine in asthma via its stimulation of cell surface adenosine receptors and subsequent downstream signalling pathway are a function of a local concentration of adenosine. (Handbook of Experimental Pharmacology, *Adenosine receptors in Health and Disease*, Vol 193, page 239-362). Adenosine acting on adenosine receptors induces the releasing of inflammatory mediators that are important in the pathogenesis of airway remodelling in asthmatics. There are several studies suggesting the potential of the adenosine $A_{2B}$ receptor antagonists for the treatment of asthma (Landells L J, et al, *The role of adenosine receptors in the action of theophylline on human peripheral blood mononuclear cells from healthy and asthmatic subjects*. Br. J. Pharmacol 129: 1140-1144, 2000).

Studies have been published demonstrating the effect of $A_{2B}$ adenosine receptor antagonists over mice deficient in adenosine-deaminasa (ADA). These studies show that mice treated with $A_{2B}$ adenosine receptor antagonist have less pulmonary inflammation, less fibrosis and greater alveolar airspace enlargement than non-treated mice, thus suggesting that $A_{2B}$ adenosine receptor signalling is a pathway critical for pulmonary inflammation and injury in vivo. (*Role of $A_{2B}$ adenosine receptor signalling in adenosine-dependent pulmonary inflammation and injury*, The Journal of Clinical Investigation, Volume 116, Number 8, August 2006, page 2173-2182; *Adenosine signalling pathways as potential therapeutic targets in respiratory disease*, Expert Opin. Ther. Targets (2013) 17(7):761772 and references therein).

A recent study has demonstrated that in a guinea pig model of asthma, the animals pre-treated with an $A_{2B}$ adenosine receptor antagonist improved the changes in tracheal responsiveness, total white blood cell and lung pathological changes. Said results showed a preventive effect of $A_{2B}$ adenosine receptor antagonist on ovalbumin-induced asthma. (*The effect of adenosine $A_{2A}$ and $A_{2B}$ antagonists on tracheal responsiveness, serum levels of cytokines and lung inflammation in guinea pig model of asthma*, Advanced Pharmaceutical Bulletin, 2014, 4(2), 131-138 and references therein).

Another recent study states that $A_{2B}$ adenosine receptor in humans would mediate indirectly the bronchoconstriction in response to adenosine and would play the main role in adenosine-induced airway inflammation and hyperactivity. Antagonists to this receptor would likely limit adenosine pro-inflammatory effects. (Cicala, C., Ialenti, A., *Adenosine signaling in airways: Toward a promising antiasthmatic approach*. Eur J Pharmacol (2013),).

b) Chronic Obstructive Pulmonary Disease (COPD)

The chronic obstructive pulmonary disease (COPD) is a heterogeneous disease that is characterized by airflow obstruction which is not fully reversible.

There are studies demonstrating that the levels of $A_{2B}$ adenosine receptors are elevated in surgical lung biopsies in patients with severe COPD. In addition, it was determined that mediators that are regulated by said receptor were elevated in the studied samples and activation of $A_{2B}$ receptors on cell isolated from the airways of COPD patients was shown to directly induce the production of these mediators, therefore suggesting that patients suffering COPD may benefit from adenosine based therapeutics, such as treatment with $A_{2B}$ adenosine receptor antagonist. (Zhou Y, et al, *Alterations in Adenosine Metabolism and Signaling in Patients with Chronic Obstructive Pulmonary Disease and Idiopathic Pulmonary Fibrosis.* 2010, PLoS ONE 5(2): e9224. doi:10.1371/journal.pone.0009224; Varani K et al, *Alteration of adenosine receptors in patients with chronic obstructive pulmonary disease.* Am J Respir Crit Care Med. 2006 Feb. 15: 173 (4):398-406).

c) Pulmonary Hypertension

Pulmonary hypertension (PH) was initially classified as primary (idiopathic) or secondary, depending on the presence or absence of identifiable causes as risk factors. The current classification was adopted in 2008 and include five groups. See, for example, Simonneau et al, *Updated clinical classification of pulmonary hypertension,* 2009, J Am Coll Car dio, 54(1):543-54.

A variety of factors contributes to the pathogenesis of PH including proliferation of pulmonary cells that can contribute to vascular remodelling. For example, pulmonary vascular remodelling occurs primarily by proliferation of arterial endothelial cells and smooth muscle cells of patients with PH. (Steiner, et al., *Interleukin-6 overexpression induces pulmonary hypertension,* 2009, Circ. Res.).

Several studies have demonstrated the proliferation of pulmonary cells, cytokines, growth factors and chemokines in serum and/or lungs of patients. These altered expressions indicate a possible inflammatory mechanism or mediation in the pathogenesis of the disease. For example, it has been demonstrated that growth factor endotheline-1 (ET-1) and inflammatory cytokine interleukin (IL-6) are elevated in serum and lungs of PH patients. (A. Giaid, et al, 1993, *Expression of endothelin-1 in the lungs of patients with pulmonary hypertension,* N. Engl. J. Med, 329(26): 1967-8 and Steiner, et al., *Interleukin-6 overexpression induces pulmonary hypertension,* 2009, Circ. Res.).

Others authors relate the role of $A_{2B}$ adenosine receptors in pulmonary hypertension, identifying a new mechanism of progression of the disease and supporting the development of new $A_{2B}$ adenosine receptor antagonists for the treatment of this disease, for example associated to interstitial lungs diseases. (Karmouty-Quintana, H et al, *The $A_{2B}$ adenosine receptor modulates pulmonary hypertension associated with interstitial lung disease.* 2012, FASEB J. June; 26(6): 2546-2557).

Other studies suggest the use of $A_{2B}$ receptors antagonists in animal models with the phenotype of PH, and that said antagonists are able to halt damages to the animal lungs. (Karmouty-Quintana H, et al., *ADORA2B and Hyaluronan modulate Pulmonary Hypertension associated with Chronic Obstructive Pulmonary Disease,* July 2013).

d) Idiopathic Pulmonary Fibrosis (IPF)

Idiopathic pulmonary fibrosis (IPF) is characterized by insidious onset of dyspnea or cough. However, a subset of patients has a short duration of symptoms with rapid progression to end-stage disease.

A recent study evidenced that partially adenosine deaminase-deficient mice showed upregulation of $A_{2B}$ adenosine receptor exhibiting spontaneous and progressive pulmonary fibrosis and died from respiratory distress. (Chunn JL et al, *Partially adenosine deaminase-deficient mice develop pulmonary fibrosis in association with adenosine elevations,* Am J Physiol Lung Cell Mol Physiol. 2006 March; 290 (3):L57987). The above results suggest a potential regulatory role for adenosine or its receptors in IPF. (Selman M et al, *Accelerated Variant of Idiopathic Pulmonary Fibrosis: Clinical Behaviour and Gene Expression Pattern,* 2007, PLoS ONE 2(5) and references therein).

Other studies have demonstrated that adenosine $A_{2B}$ receptors might play a role in the pathogenesis of interstitial fibrosis, among others chronic pulmonary diseases, likely due to the capacity of adenosine $A_{2B}$ receptors to stimulate IL-6 production, and that these receptors can stimulate the fibrosis indirectly in the lung. (Cronstein, BN, 2011, *Adenosine receptors and fibrosis: a translational review,* F1000 Biology Reports 2011, 25 3:21). Moreover, it has been demonstrated the protective effect of $A_{2B}$ adenosine receptor antagonist on pulmonary fibrogenesis, verifying said effect in the bleomycin-induced pulmonary fibrosis model; which suggests that $A_{2B}$ adenosine receptor antagonist may be a novel therapeutic option in the treatment of pulmonary fibrosis. (Edwin SL et al, *Adenosine in fibrosis,* Mod Rheumatol. 2010 April; 20(2): 114-122).

Potential of Adenosine $A_{2B}$ Receptor Antagonists in Oncology

The adenosine receptors are found to be upregulated in various tumour cells. Activation of the receptors by specific ligands, agonists or antagonists, modulate tumour growth via a range of signalling pathways. Specifically, the $A_{2B}$ adenosine receptor is not stimulated under physiological levels of adenosine, but may therefore play an important role in conditions associated with high level or massive release of adenosine, such as those occurring in ischemia or presence of tumours, where hypoxia is commonly observed. Currently several mechanisms have been described by which $A_{2B}$ adenosine receptor might be involved in tumour development and progression. (Fishman P et al, *Adenosine Receptors and Cancer,* Handb Exp Pharmacol. 2009; (193): 399-441).

For example, in the case of breast cancer, it has been described that antagonists $A_{2B}$ adenosine receptors have a toxic effect over breast tumour cells overexpressing Fos-related antigen-1 (Fra-1), a key antigen in metastasis development in breast cancer. (Desmet C J et al, *Identification of a pharmacologically tractable Fra-1/ADORA2B axis promoting breast cancer metastasis,* PNAS, Mar. 26, 2013, vol. 110, no. 13, page 15 5139-5144).

Additionally, there are studies suggesting that selective $A_{2B}$ adenosine receptors might be useful as potential novel therapeutics in inhibition growth of prostate cancer cells. (Wei Q et al, *$A_{2B}$ adenosine receptor blockade inhibits growth of prostate cancer cells,* Purinergic Signalling (2013), 9:271-280).

Related to melanoma, emerging evidences suggest that $A_{2B}$ adenosine receptor is implicated in tumour progression in some murine tumour models. For example, it has been evidenced that pharmacological blockade of $A_{2B}$ receptor reversed immune suppression in the tumour microenvironment, leading to a significant delay in melanoma growth; pointing out that $A_{2B}$ adenosine receptor antagonists could be useful as adjuvants in the treatment of melanoma. (Iannone, R et al, *Therapeutic Potential of PSB1115 in Melanoma,* Neoplasia Vol. 15, No. 12, 2013).

Potential of Adenosine $A_{2B}$ Receptor Antagonists in Metabolic Disorders

In the case of metabolic disorders, for example in obesity, studies show the role of the $A_{2B}$ adenosine receptor in mediating of metabolic homeostasis, correlating the results with obese patients, and identifying the $A_{2B}$ adenosine receptor as a significant regulator in high cholesterol diet induced hallmarks of type-II diabetes, thereby pointing its therapeutic potential. (Johnston-Cox H, et al, *The $A_{2B}$ Adenosine Receptor Modulates Glucose Homeostasis and Obesity*. 2012. PLoS ONE 7(7): e40584; Volpini R, et al, *Medicinal chemistry and pharmacology of $A_{2B}$ adenosine receptors*. Curr Top Med Chem 3: 427-443, 2003).

Other studies state that adenosine and adenosine receptor are involved in glucose homeostasis. Nowadays, it has been established that said receptors are reasonable targets for anti-diabetic therapy. In particular, the $A_{2B}$ adenosine receptor antagonists have showed an anti-diabetic potential mainly by increasing plasma insulin levels under conditions when the adenosine tonus was elevated in vivo and increased insulin release in vitro. (Rusing, D et al, *The impact of adenosine and $A_{2B}$ receptors on glucose homeostasis*, J Pharm Pharmacol. 2006 December; 58(12):1639-45).

Potential of Adenosine $A_{2B}$ Receptor Antagonists in Central Nervous System

Recently, it has been suggested that $A_{2B}$ adenosine receptor modulates different physiological and pathological processes in the brain, basing its therapeutic role in the low affinity of said receptor to adenosine, since said receptor is activated when adenosine levels reach concentrations of micromolar order, so especially in the progression of neurodegenerative diseases, may play an important role. (Popoli, P, Pepponi, R, *Potential Therapeutic Relevance of Adenosine $A_{2B}$ and $A_{2A}$ Receptors in the Central Nervous System*, CNS & Neurological Disorders-Drug Targets, 2012, Volume 11, Number 6, September 2012, pp. 664-674(11)). Other study suggests the potential of the adenosine $A_{2B}$ receptor antagonists for the treatment of Alzheimer's disease (Rosi S, et al, *The influence of brain inflammation upon neuronal adenosine $A_{2B}$ receptors*. J Neurochem 86: 220-227, 2003).

Potential of Ligands of $MT_3$ Melatonin Receptor in the Treatment of Various Pathologies The $MT_3$ melatonin receptor was discovered in 1988 by Duncan et al ((Duncan M J, et al, (1988). *2-[125I] iodomelatonin binding sites in hamster brain membranes: pharmacological characteristics and regional distribution*. Endocrinology 122:1825-1833). Said receptor has a low affinity to melatonin, in comparison with the other two receptors $MT_1$ and $MT_2$.

Currently, is well know the key role of the melatonin in many physiopathological phenomena and in the control of circadian rhythm; however, the melatonin has a short half-life therefore is rapidly metabolised. Therefore, it is necessary to provide melatonin analogues more stable and with therapeutic effect superiors to the hormone itself.

At present, is known that ligands of melatoninergic systems have important pharmacologic properties in respect of the central nervous system as anxiolytics and anti-psychotics drugs (Lewis A J, et al, *Neuropharmacology of pineal secretions*, Drug Metabol Drug Interact. 1990; 8 (3-4): 247-312), for the treatment of Parkinson's disease (Erlich, S S et al, *The pineal gland: anatomy, physiology, and clinical significance*, J Neurosurg, 1985, 63, 321-341) and for the treatment of Alzheimer's disease (Skene, D J et al, *Daily variation in the concentration of melatonin and 5-methoxytryptophol in the human pineal gland: effect of age and Alzheimer's disease*, Brain Research, 1990, Sep. 24, 528 (1): 170-4).

These compounds have also demonstrated activity in relation to certain cancers (Melatonin-Clinical Perspectives, Oxford University Press, 1988, pp. 164-165), diabetes (Clinical Endocrinology, 1986, 24, pp. 359-364), and in the treatment of obesity (International Journal of Eating Disorders, 1996, 20 (4), pp. 443-446).

As said before, melatonin is implicated in both biorhythm synchronization and neuroprotection from oxidative stress. Currently several studies link the $MT_3$ melatonin receptor with the enzyme quinone reductase 2 ($QR_2$). (Boutin J A et al, *5 Studies of the melatonin binding site location onto quinone reductase 2 by directed mutagenesis*, Arch Biochem Biophys. 2008 Sep. 1; 477(1):12-9 and references therein), (Nosjean, O et al, *Identification of the melatonin-binding site $MT_3$ as the quinone reductase 2*, J Biol Chem.2000 Oct. 6; 275 (40):31311-7).

The enzyme $QR_2$ is a cytosolic flavoprotein that catalyzes the reduction of its substrates and enhances the production of damaging activated quinones and reactive oxygen species. Several published studies have demonstrated that enzyme $QR_2$ is in altered high levels in patients suffering neurological disorders, such as Parkinson disease (Fu, Y et al, *Quinone Reductase 2 Is a Catechol Quinone Reductase*, Biol Chem. 2008 Aug. 29; 283(35): 23829-23835) and Alzheimer disease, showing in that case that patients suffering the disease have notably higher enzyme levels than controls subjects, suggesting the role of the enzyme in the progression of the disease, due to an increase in toxic quinone levels and consequent loss of cognitive function (Hashimoto, T et al, *Increased hippocampal quinone reductase 2 in Alzheimer's disease*, Neurosci Lett. 2011 Sep. 8; 502(1):10-2).

In a recent study, it has been demonstrated the overexpression of quinone reductase 2 in animal models of learning deficits and induced amnesia. The enzyme $QR_2$ is a cytosolic flavoprotein that catalyzes the reduction of its substrates and enhances the production of damaging activated quinone and reactive oxygen species (ROS), which is associated with deficits in learning and memory with age as well as in Alzheimer's disease. Adults $QR_2$ knock-out mice showed enhanced learning abilities in various task, suggesting a role for $QR_2$ in cognitive behaviours which make $QR_2$ inhibitors possibly a novel therapeutic strategy toward the treatment of learning deficits especially observed in the aged brain. (Benoit C E et al, *Loss of quinone reductase 2 function selectively facilitates learning behaviours*, 2010, The Journal of Neuroscience, September 22, 30(38):12690-12700 and reference therein).

Others authors have published the effect of resveratrol, a polyphenolic compound found in grapes, red wine, peanuts, and others, over the $QR_2$ enzyme, on the treatment of bleomycin-induced pulmonary fibrosis, demonstrating that tissue total antioxidant capacity is reduced by bleomycin compared with control group and increased by resveratrol, thereby providing evidence that resveratrol has promising potential in the treatment of bleomycin-induced pulmonary fibrosis in rats. (Akgedik, R et al, *Effect of Resveratrol on Treatment of Bleomycin-Induced Pulmonary Fibrosis in Rats*, Inflammation, Vol. 35, No. 5, October 2012).

A recent study demonstrated that the inhibition of quinone reductase 2 by resveratrol may protect cells against several pathologic processes associated to cancer (St John S E et al, *Design, synthesis, biological and structural evaluation of functionalized resveratrol analogues as inhibitors of quinone reductase 2*, Bioorg Med Chem. October 1; 21(19): 6022-37, 2013).

Other studies have suggested that quinone reductase 2 could play an important role in the regulation of catecholamine oxidation process that may be involved in the etiology of Parkinson disease. (Fu, Y et al, *Quinone Reduc-* tase 2 Is a Catechol Quinone Reductase, Biol Chem. 2008 Aug. 29; 283(35): 23829-23835).

In connection with the patent literature, there are documents disclosing new compounds as adenosine $A_{2B}$ receptors antagonists. For example, the patent application WO 2006/044610 discloses a method for the treatment and prevention of airway remodelling and/or pulmonary inflammation by administration of $A_{2B}$ receptor antagonist to a mammal that is genetically or environmentally predisposed to the above diseases. It has been demonstrated that the adenosine $A_{2B}$ receptors antagonists of WO 2006/044610 inhibit the pulmonary inflammation and reduce the number of inflammatory cells as well as pro-inflammatory cytokines and chemokines in bronchoalveolar lavage fluid. Therefore, these findings provided powerful support to the hypothesis that $A_{2B}$ receptor antagonists might be promising therapeutic agents in the treatment of not only asthma and COPD, but also pulmonary fibrosis.

Another document, patent application WO 2005/070926, discloses aminothiazole dual $A_{2B}/A_3$ receptor antagonists, useful for the treatment of a condition mediated by activation of adenosine $A_{2B}$ receptor.

Others authors have suggested the application of $A_{2B}$ adenosine receptors antagonists for the treatment of neurological disorders, such as Alzheimer's disease, hypervascularization, type I hypersensitivity disorders. (WO 2004/106337, WO 2006/138376).

On the other hand, patent application WO 2005/012282 disclose compounds useful in the treatment of disorders of the melatoninergic system, such as stress, cardiovascular diseases, Parkinson disease, Alzheimer's disease, obesity, diabetes, so on. The compounds disclosed in said application exhibited a high affinity for melatonin receptors and a significant selectivity for $MT_3$-type sites. Different types of compounds with similar activities are described in patent documents EP 1 466 604, FR 2 823 153 and FR 2 821 843.

Compounds possessing both $MT_3$ receptor inhibition activity and $A_{2B}$ antagonist activity are highly desirable since such bifunctional compounds would ameliorate diseases known to be susceptible to improvement by treatment with an antagonist of the $A_{2B}$ adenosine receptor and also known to be susceptible to improvement by inhibition of the $MT_3$ melatonin receptor, through two independent modes of action while having single molecule pharmacokinetics. This could yield increased efficacy with similar therapeutic index (i.e. the amount of therapeutic agent that causes therapeutic effect to the amount that causes toxicity) to the single agents or similar efficacy with superior therapeutic index.

Examples of diseases known to be susceptible to improvement by treatment with an antagonist of the $A_{2B}$ adenosine receptor and also known to be susceptible to improvement by inhibition of the $MT_3$ melatonin receptor are respiratory diseases such as pulmonary fibrosis, neurological disorders such as Alzheimer Disease, metabolic disorders such as diabetes type II and cancer.

Additionally compounds of the present invention are potent adenosine $A_{2B}$ receptor antagonists and potent melatonin $MT_3$ ligands.

SUMMARY OF THE INVENTION

In one of its aspects (aspect 1), the present invention refers to pyridine derivatives of formula (I):

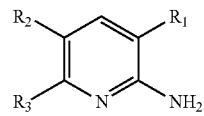

wherein:
  $R^1$ represents a hydrogen atom or a halogen atom;
  $R^2$ represents a six-membered heteroaryl ring optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy groups;
  $R^3$ represents a six-membered heteroaryl ring optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy groups;
  N-oxides of said compounds and pharmaceutically acceptable salts thereof, with the proviso that compound of formula (I) is not:
  5-(pyridin-4-yl)-6-(pyridin-4-yl)pyridin-2-amine
  5-(pyridin-3-yl)-6-(pyridin-3-yl)pyridin-2-amine
  5-(pyrazin-2-yl)-6-(pyridin-4-yl)pyridin-2-amine
  5-(4-methylpyridin-2-yl)-6-(pyridin-4-yl)pyridin-2-amine Other aspects of the present invention are:
Aspect 2) processes for the preparation of the compounds of aspect 1.
Aspect 3) pharmaceutical compositions comprising an effective amount of a compound of aspect 1.
Aspect 4) pharmaceutical compositions according to aspect 3 further comprising a therapeutically effective amount of Pirfenidone, Nintedanib, the LPA1 antagonist AM152, dopamine agonists such as L-Dopa, Ropinirole or Pramipexole, inhibitors of Monoxygenase B (MAO-B) enzyme such as Selegiline or Rasagiline or inhibitors of acetylcholinesterase enzyme such as Galantamine, Rivastigmine, Donepezil and Tacrine.
Aspect 5) the use of the compounds of aspect 1 in the manufacture of a medicament, in particular for treating diseases that can be ameliorated by antagonism of the adenosine $A_{2B}$ receptor and/or by inhibition of $MT_3$ melatonin receptor.
Aspect 6) methods for the treatment of diseases that can be ameliorated by antagonism of the adenosine $A_{2B}$ receptor and/or by inhibition of $MT_3$ melatonin receptor by administration of the compounds of aspect 1 or the pharmaceutical compositions of aspect 2 or 3 to a subject in need of said treatment.
Aspect 7) combination product of compounds of aspect 1 with one more therapeutic agent selected from Pirfenidone, Nintedanib. the LPA1 antagonist AM152, dopamine agonist such as L-Dopa, Ropinirole or Pramipexole, inhibitors of Monoxygenase B (MAO-B) enzyme such as Selegiline or Rasagiline or inhibitors of acetylcholinesterase enzyme such as Galantamine, Rivastigmine, Donepezil and Tacrine.
Aspect 8) A compound as defined in aspect 1 for use as a medicament.
Aspect 9) A compound as defined in aspect 1 for use in the treatment of a disease or pathological condition selected from the group consisting of asthma, chronic obstructive pulmonary disease, idiopathic pulmonary fibrosis, obesity, diabetes, atherosclerosis, senile dementia, Alzheimer's disease, Parkinson's disease and cancer.

As it is said before, the pyridine derivatives of the invention are useful in the treatment or prevention of diseases known to be susceptible to amelioration by treatment with antagonist of $A_{2B}$ adenosine receptor and/or by inhibition of $MT_3$ melatonin receptor. Such diseases are, for example, acute or chronic respiratory diseases, such as asthma, chronic obstructive pulmonary disease and idiopathic pulmonary fibrosis disease, metabolic disorders, such as obesity, diabetes and atherosclerosis, cancer and neurological disorders, such as senile dementia, Alzheimer's disease and Parkinson's disease.

Accordingly, the derivatives of the present invention and pharmaceutically acceptable salts or N-oxides thereof, and pharmaceutical compositions comprising such compounds and/or salts thereof, may be used in a method of treatment of pathological conditions or disease of human body which comprises administering to a subject in need of said treatment, an effective amount of the pyridine derivatives of the invention or a pharmaceutically acceptable salt thereof.

As used herein, the term halogen atom comprises chlorine, fluorine, bromine or iodine atom, preferably fluorine, chlorine or bromine atom. The term halo when used as a prefix has the same meaning.

As used herein, the term haloalkyl is used to designate $C_1$-$C_4$ alkyl substituted by one or more halogen atoms, preferably one, two or three halogen atoms. The haloalkyl groups may be linear or branched. Preferably, the halogen atoms are selected from the group consisting of fluorine or chlorine atoms. In a preferred embodiment, the haloalkyl groups are $C_1$-$C_4$ alkyl substituted by one, two or three fluorine or chlorine atoms.

As used herein the term $C_1$-$C_6$ alkyl is used to designate linear or branched hydrocarbon radicals ($C_nH_{2n+1}$) having 1 to 6 carbon atoms. Examples include methyl, ethyl, n-propyl, i-propyl, n-butyl, sec-butyl, tert-butyl, n-pentyl, 1-methyl-butyl, 2-methyl-butyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3dimethylbutyl, 2,2-dimethylbutyl, 2,3-dimethylbutyl, 2-methylpentyl and 3-methylpentyl radicals. In a preferred embodiment said alkyl groups have 1 to 4 carbon atoms.

As used herein, the term cycloalkyl embraces hydrocarbon cyclic groups having 3 to 12 carbon atoms. Said cycloalkyl groups may have a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3trimethylbicyclo[2.2.1]hept-2-yl, (2,3,3-trimethylbicyclo [2.2.1]hept-2-yl).

Carbocyclic groups as defined in the above paragraph which are fused with an aryl group, for example indane, and the like are considered to be encompassed within the definition of the term cycloalkyl.

As used herein, the term C alkoxy is used to designate radicals which contain a linear or branched $C_1$-$C_6$ alkyl group linked to an oxygen atom ($C_nH_{2n+1}$—O—). Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy or 2-hydroxypropoxy.

As used herein the term cycloalkoxy is used to designate radicals containing a $C_3$-$C_{12}$ cycloalkyl groups linked to an oxygen atom.

As used herein, the term six-membered heteroaryl ring is used to designate a 6-membered heteroaromatic ring containing carbon, hydrogen and one or more nitrogen atoms. Said radicals may optionally be substituted by one or more substituents selected from the group consisting of halogen, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy groups. The preferred radicals are optionally substituted pyridyl and pyrimidinyl. When a heteroaryl radical carries 2 or more substituents, the substituents may be the same or different.

As used herein, some of the atoms, radicals, chains or cycles present in the general structures of the invention are "optionally substituted". This means that these atoms, radicals, chains or cycles can be either unsubstituted or substituted in any position by one or more, for example 1, 2, 3 or 4, substituents, whereby the hydrogen atoms bound to the unsubstituted atoms, radicals, chains or cycles are replaced by chemically acceptable atoms, radicals, chains or cycles. When two or more substituents are present, each substituent may be the same or different.

As used herein, the term pharmaceutically acceptable salt is used to designate salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium), alkali earth metal (e.g. calcium or magnesium) hydroxides, and organic bases, for example alkyl amines, arylalkyl amines and heterocyclic amines.

Other preferred salts according to the invention are quaternary ammonium compounds wherein an equivalent of an anion ($X^{-n}$), wherein "–n" indicates the negative charge of the anion and is typically –1, –2 or –3, is associated with the positive charge of the N atom. $X^{-n}$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and ptoluenesulphonate. $X^{-n}$ is preferably an anion selected from chloride, bromide, iodide, sulphate, nitrate, acetate, maleate, oxalate, succinate or trifluoroacetate. More preferably, X– is chloride, bromide, trifluoroacetate or methanesulphonate.

According to one embodiment of the present invention in the compounds of formula (I), $R^1$ represents a halogen or hydrogen atom. In a preferred embodiment, $R^1$ represents a halogen atom. In a more preferred embodiment, $R^1$ represents a chlorine or bromine atom.

According to another embodiment of the present invention in the compounds of the formula (I) $R^2$ represents a six-membered heteroaryl ring optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy.

In a more preferred embodiment, $R^2$ represents a six-membered heteroaryl ring having one or two nitrogen atoms, optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy.

In another preferred embodiment, $R^2$ represents a pyridyl group optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy.

In a more preferred embodiment, $R^2$ represents a 4-pyridyl group optionally substituted by halogen atom. In a more preferred embodiment, $R^2$ represents a fluoro-pyridyl group optionally further substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy.

According to another embodiment of the present invention in the compounds of formula (I) $R^3$ represents a six-membered heteroaryl ring optionally substituted by one or more substituents selected from the group consisting of halogen atom, $C_1$-$C_4$ haloalkyl, linear or branched $C_1$-$C_6$ alkyl, linear or branched $C_3$-$C_{12}$ cycloalkyl, $C_1$-$C_6$ alkoxy and $C_3$-$C_{12}$ cycloalkoxy.

In a preferred embodiment, $R^3$ represents a six-membered heteroaryl ring having one or two nitrogen atoms, optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy.

In a more preferred embodiment, $R^3$ represents a group selected from pyridyl and pyrimidinyl group optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy.

In a more preferred embodiment, $R^3$ represents a group 3-pyridyl or 4-pyridyl optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy.

In a more preferred embodiment, $R^3$ represents a group 3-pyridyl or 4-pyridyl optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy. In a further preferred embodiment of the present invention in the compounds of formula (I), $R^1$ represents a chlorine or bromine atom, $R^2$ represents a 4-pyridyl group optionally substituted by one or two fluorine atoms and $R^3$ represents a group 3-pyridyl or 4-pyridyl optionally substituted by one or more substituents selected from the group consisting of halogen atom, $C_1$-$C_4$ haloalkyl, linear or branched $C_1$-$C_6$ alkyl and linear or branched $C_1$-$C_6$ alkoxy.

Particular individual compounds of the present invention include:

5-(pyridin-4-yl)-6-(pyrimidin-5-yl)pyridin-2-amine,
5-(3-fluoropyridin-4-yl)-6-(pyrimidin-5-yl)pyridin-2-amine,
6-(pyridin-3-yl)-5-(pyridin-4-yl)pyridin-2-amine,
5-(3-fluoropyridin-4-yl)-6-(pyridin-3-yl)pyridin-2-amine,
6-(pyridin-3-yl)-5-(pyrimidin-5-yl)pyridin-2-amine,
6-(5-fluoropyridin-3-yl)-5-(3-fluoropyridin-4-yl)pyridin-2-amine,
5-(3-fluoropyridin-4-yl)-6-(5-methoxypyridin-3-yl)pyridin-2-amine,
6-[5-(trifluoromethy)pyridin-3-yl]-5-(3-fluoropyridin-4-yl)pyridin-2-amine,
6-(5-chloropyridin-3-yl)-5-(3-fluoropyridin-4-yl)pyridin-2-amine,
5-(3-fluoropyridin-4-yl)-6-(6-methoxypyridin-3-yl)pyridin-2-amine,
5-(3-fluoropyridin-4-yl)-6-(pyridin-4-yl)pyridin-2-amine,
5,6-bis-(3-fluoropyridin-4-yl)pyridin-2-amine,
5-(3-chloropyridin-4-yl)-6-(pyridin-3-yl)pyridin-2-amine,
5-(3-chloropyridin-4-yl)-6-(pyridin-4-yl)pyridin-2-amine,
5-(2-chloro-6-methylpyridin-4-yl)-6-(pyridin-3-yl)pyridin-2-amine,
5-(2-methoxypyridin-4-yl)-6-(pyridin-3-yl)pyridin-2-amine,
3-chloro-5-(pyridin-4-yl)-6-(pyrimidin-5-yl)pyridin-2-amine,
3-bromo-5-(pyridin-4-yl)-6-(pyrimidin-5-yl)pyridin-2-amine,
3-chloro-5-(3-fluoropyridin-4-yl)-6-(pyrimidin-5-yl)pyridin-2-amine,
3-bromo-5-(3-fluoropyridin-4-yl)-6-(pyrimidin-5-yl)pyridin-2-amine,
3-chloro-6-(pyridin-3-yl)-5-(pyridin-4-yl)pyridin-2-amine,
3-bromo-6-(pyridin-3-yl)-5-(pyridin-4-yl)pyridin-2-amine,
3-chloro-5-(3-fluoropyridin-4-yl)-6-(pyridin-3-yl)pyridin-2-amine,
3-bromo-5-(3-fluoropyridin-4-yl)-6-(pyridin-3-yl)pyridin-2-amine,
3-chloro-6-(pyridin-3-yl)-5-(pyrimidin-5-yl)pyridin-2-amine,
3-bromo-6-(pyridin-3-yl)-5-(pyrimidin-5-yl)pyridin-2-amine,
3-chloro-6-(5-fluoropyridin-3-yl)-5-(3-fluoropyridin-4-yl)pyridin-2-amine,
3-bromo-6-(5-fluoropyridin-3-yl)-5-(3-fluoropyridin-4-yl)pyridin-2-amine,
3-chloro-5-(3-fluoropyridin-4-yl)-6-(5-methoxypyridin-3-yl)pyridin-2-amine,
3-bromo-5-(3-fluoropyridin-4-yl)-6-(5-methoxypyridin-3-yl)pyridin-2-amine,
3-chloro-6-[5-(trifluoromethyl)pyridin-3-yl]-5-(3-fluoropyridin-4-yl)pyridin-2-amine,
3-bromo-6-[5-(trifluoromethyl)pyridin-3-yl]-5-(3-fluoropyridin-4-yl)pyridin-2-amine,
3-chloro-6-(5-chloropyridin-3-yl)-5-(3-fluoropyridin-4-yl)pyridin-2-amine,
3-chloro-5-(3-fluoropyridin-4-yl)-6-(pyridin-4-yl)pyridin-2-amine,
3-bromo-5-(3-fluoropyridin-4-yl)-6-(pyridin-4-yl)pyridin-2-amine,
3-chloro-5-(3-fluoropyridin-4-yl)-6-(6-methoxypyridin-3-yl)pyridin-2-amine,
3-bromo-5-(3-fluoropyridin-4-yl)-6-(6-methoxypyridin-3-yl)pyridin-2-amine,
3-chloro-5,6-bis-(3-fluoropyridin-4-yl)pyridin-2-amine,
3-chloro-5-(3-chloropyridin-4-yl)-6-(pyridin-3-yl)pyridin-2-amine,
3-chloro-5-(3-chloropyridin-4-yl)-6-(pyridin-4-yl)pyridin-2-amine,
3-chloro-5-(2-chloro-6-methylpyridin-4-yl)-6-(pyridin-3-yl)pyridin-2-amine,
3-chloro-5-(2-methoxypyridin-4-yl)-6-(pyridin-3-yl)pyridin-2-amine.

The compounds of this invention can be prepared by using the procedures described below. To facilitate the description of the procedures, concrete examples have been used but they do not restrict in any way the scope of the present invention. The synthesis of compound of formula (I) is outlined in scheme 1.

Scheme 1

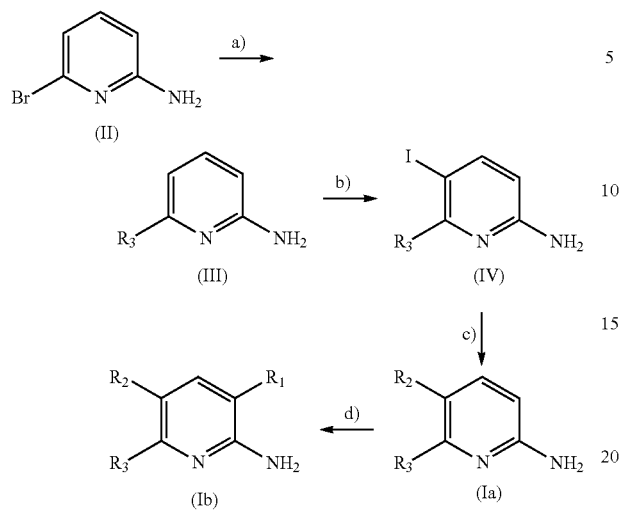

In the above scheme, compounds of formula (Ia) are compounds according to the present invention wherein $R^1$ is a hydrogen atom, and compounds of formula (Ib) are compounds according to the present invention wherein $R^1$ is a halogen atom. Moreover, $R^2$ and $R^3$ are groups according to have been defined to the compounds of the present invention, i.e., six-membered heteroaryl rings optionally substituted.

Reagents and Conditions:
Step a) boronic acid or boronate derivative of $R^3$, Pd(dppf)Cl$_2$.CH$_2$Cl$_2$, Cs$_2$CO$_3$, Dioxane/H$_2$O, 24 h, 100° C.
Step b) NIS, AcOH, room temperature.
Step c) boronic acid or boronate derivative of $R^2$, Pd(dppf)Cl$_2$.CH$_2$Cl$_2$, Cs$_2$CO$_3$, Dioxane/H$_2$O, 24 h, 100° C.
Step d) NCS or NBS or NIS or Selecfluor® DMF, room temperature.

Derivatives of general formula (I) are prepared in several stages from commercially available 6-bromopyridin-2-amine derivatives of (II), according to Scheme 1. The starting reagent (II) is reacted by a Suzuki-type coupling with boronic acid or boronate derivative of $R^3$ using a palladium catalyst such as [1,1'Bis(diphenylphosphino)ferrocene] dichloropalladium (II), complex with dichloromethane (Pd/dppf)Cl$_2$.CH$_2$Cl$_2$) in dioxane in the presence of an aqueous solution of a base such as cesium carbonate and at temperature between 25° C. and 110° C. to provide compounds of formula (III). Iodation of derivative (III) using N-iodosuccinimide (NIS) in polar solvents such as glacial acetic acid and temperatures ranging from 0° C. to 50° C. yields compounds of formula (IV). These products are reacted by further Suzuki-type coupling similar to first step with a corresponding boronic acid or boronate derivative of $R^2$ under the standard procedures for palladium catalysed reaction describe above to give compounds of formula (Ia), which also are object of the present invention when $R^1$ represents a hydrogen atom. Following halogenation of derivative (Ia) using halogenating agent, (such as N-chlorosuccinimide (NCS), N-bromosuccinimide (NBS), N-iodosuccinimide (NIS), 1-fluoro-4-methyl-1,4-diazoniabicyclo[2.2.2]octane bis(tetrafluoroborate) and 1-(chloromethyl)-4-fluoro-1,4-diazoniabicyclo[2.2.2]octane, bis(tetrafluoroborate=(Selecfluor®), in polar aprotic solvents such as DMF and temperatures ranging from 0° C. to 50° C. provides compounds of formula (Ib), which are the object of the present invention.

To synthetized the compounds of formula (I) when $R^2$=$R^3$, the reactions described above in Scheme 2 can be used.

Scheme 2

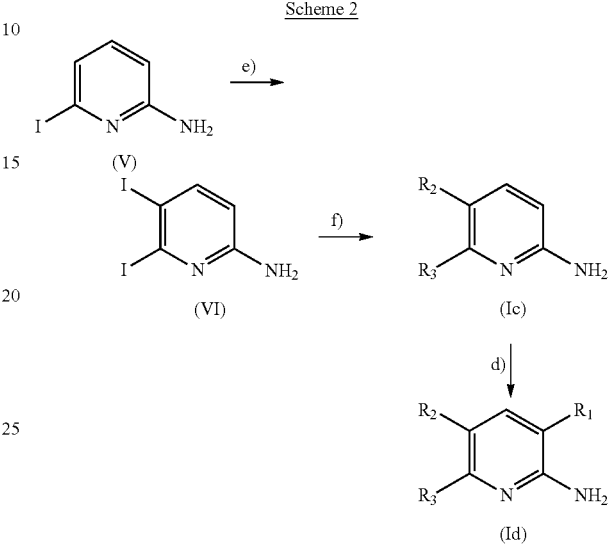

In the above scheme, compounds of formula (Ic) are compounds according to the present invention wherein $R^1$ is a hydrogen atom, and compounds of formula (Id) are compounds according to the present invention wherein $R^1$ is a halogen atom. Moreover, the groups $R^2$ and $R^3$ are groups according to have been defined to the compounds of the present invention, i.e., six-membered heteroaryl rings optionally substituted, but with the proviso that both groups are the same.

Reagents and Conditions:
Step e): NIS, DMF, room temperature.
Step f): boronic acid or boronate derivative of $R^2$ ($R^2$ being equal to $R^3$), Pd(dppf)Cl$_2$.CH$_2$Cl$_2$, Cs$_2$CO$_3$, Dioxane/H$_2$O, 24 h, 100° C.
Step d): NCS or NBS, DMF, room temperature Compounds of formula (VI) are obtained by iodation of derivative (V) using N-iodosuccinimide in DMF and temperatures ranging from 0° C. to 50° C. These di-iodine derivatives of formula (VI) are reacted by a standard Suzuki-type coupling with a corresponding boronic acid or boronate derivative under the standard procedures for palladium catalysed reaction described above to provide compounds of formula (Ic), which also are objects to the present invention when $R^1$ represents a hydrogen atom. The introduction of halogen atom is made in analogy to the halogenation reaction above described in reaction d) in Scheme 1 to give compounds of formula (Id) which are objects of the present invention.

Pharmacological Activity

Adenosine $A_{2B}$ Receptor Subtype Competition Radioligand Binding Assay

The binding assay for adenosine $A_{2B}$ receptor subtype was carried out on human recombinant source (HEK-293 cells) and [$^3$H]DPCPX as radioligand, according to assay disclosed by Fredholm et al. (International Union of Pharmacology. XXV. Nomenclature and classification of adenosine receptors, Pharmacol Rev. 2001December; 53(4):527-52).

Study of Binding to Melatonin $MT_3$ Binding Sites

The experiment of binding to $MT_3$ sites was carried out on hamster brain membranes using [$^{125}$I]2-iodomelatonin as radioligand in accordance with the protocol described by Pickering, D. S et al. (Pickering, D. S et al, 1990, Pharmacological characterization of melatonin binding sites in Syrian hamster hypothalamus, Eur J Pharmacol. 1990 Jan. 3; 175(1):71-7).

Results

Table 1 shows the adenosine receptor activity (Ki values) and $IC_{50}$ values of $MT_3$ melatonin receptor of some compounds of the present invention.

TABLE 1

| Compounds | Example | $hA_{2B}$,Ki (nM) | $hA_{2A}$,Ki (nM) | $IC_{50}$ $MT_3$ (nM) |
|---|---|---|---|---|
| 5-(3-fluoropyridin-4-yl)-6-(pyridin-4-yl)pyridin-2-amine | 11 | 149 | >5000 | ND |
| 3-chloro-6-(pyridin-3-yl)-5-(pyridin-4-yl)pyridin-2-amine | 21 | 34.5 | 500 | 130 |
| 3-bromo-6-(pyridin-3-yl)-5-(pyridin-4-yl)pyridin-2-amine | 22 | 46.1 | 300 | 140 |
| 3-chloro-5-(3-fluoropyridin-4-yl)-6-(pyridin-3-yl)pyridin-2-amine | 23 | 23.9 | 4800 | 98 |
| 3-bromo-5-(3-fluoropyridin-4-yl)-6-(pyridin-3-yl)pyridin-2-amine | 24 | 37 | >5000 | ND |
| 3-chloro-6-(5-fluoropyridin-3-yl)-5-(3-fluoropyridin-4-yl)pyridin-2-amine | 27 | 150 | >5000 | 250 |
| 3-chloro-5-(3-fluoropyridin-4-yl)-6-(pyridin-4-yl)pyridin-2-amine | 34 | 12 | 555 | ND |
| 3-bromo-5-(3-fluoropyridin-4-yl)-6-(pyridin-4-yl)pyridin-2-amine | 35 | 13 | 1300 | ND |
| 3-chloro-5-(3-fluoropyridin-4-yl)-6-(6-methoxypyridin-3-yl)pyridin-2-amine | 36 | 24 | >5000 | ND |

ND: Not determined

As can be seen from the results described in Table 1, the compounds of the present invention are potent adenosine $A_{2B}$ and melatonin $MT_3$ receptor antagonists showing selectivity against the adenosine $A_{2A}$ receptor.

The derivatives of the invention are useful in the treatment or prevention of diseases known to be susceptible to improvement by treatment with an antagonist of an adenosine receptor, in particular those susceptible to ameliorate by treatment with and antagonist of the $A_{2B}$ adenosine receptor and by inhibition of the $MT_3$ melatonin receptor. Such diseases are, for example respiratory diseases, metabolic disorders, neurologic disorders and cancer.

Accordingly, the derivatives of the invention and pharmaceutically acceptable salts thereof, and pharmaceutical compositions comprising such compounds and/or salts thereof, may be used in a method of treatment of disorders of the human body which comprises administering to a subject requiring such treatment an effective amount of the 2-amino pyridine derivative of the invention or a pharmaceutically acceptable salt thereof.

The present invention also provides pharmaceutical compositions which comprise, as an active ingredient, at least a 2-amino pyridine derivative of formula (I) or a pharmaceutically acceptable salt thereof in association with, others therapeutics agents a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably, the compositions are made up in a form suitable for oral, topical, nasal, rectal, percutaneous or injectable administration.

The pharmaceutically acceptable excipients, which are admixed with the active compound or salts of such compound, to form the compositions of this invention, are well known per se and the actual excipients used depend inter alia on the intended method of administering the compositions.

Compositions of this invention are preferably adapted for injectable and oral (per os) administration. In this case, the compositions for oral administration may take the form of tablets, sustained release tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents, which may be used in the preparation of the compositions, include those liquid and solid diluents, which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 2-2000 mg of active ingredient per day. Daily dosage may be administered in one or more treatments, preferably from 1 to 4 treatments, per day.

The present invention will be further illustrated by the following examples. The following are given by way of illustration and do not limit the scope of the invention in any way. The synthesis of the compounds of the invention is illustrated by the following examples including the preparation of the intermediates, which do not limit the scope of the invention in any way.

Abbreviations

In the present application are used the following abbreviations, with the corresponding definitions:
AcOH: acetic acid
DMF: dimethylformamide
DPCPX: 8-cyclopentyl-1,3-dipropylxanthine
dppf: 1,1'-Bis(diphenylphosphino)ferrocene
HEK-293: embryonic human cells of kidney 293
NBS: N-Bromosuccinimide
NCS: N-chlorosuccinimide
NIS: N-iodosuccinimide

EXAMPLES

General. Reagents, solvents and starting products were acquired from commercial sources. The term "concentration" refers to the vacuum evaporation using a Büchi rotavapor. When indicated, the reaction products were purified by "flash" chromatography on silica gel (40-63 μm) with the indicated solvent system. The spectroscopic data were measured in a Varian Mercury 400 spectrometer. The melting points were measured in a Büchi 535 instrument. The HPLC-MS were performed on a Gilson instrument equipped with a Gilson 321 piston pump, a Gilson 864 vacuum degasser, a Gilson 189 injection module, a 1/1000 Gilson splitter, a Gilson 307 pump, a Gilson 170 detector, and a Thermoquest Fennigan aQa detector.

Intermediate 1

6-bromo-5-iodopyridin-2-amine

N-iodosuccinimide (0.256 g, 1.16 mmol) was added to a solution of 6 bromopyridin-2-amine (0.2 g, 1.16 mmol) in dichloromethane (10 mL). The mixture was stirred at room temperature 2 hours. The solvent was evaporated under reduced pressure and the residue (a black solid) was obtained by washing with water. The compound washed several times with water was a beige solid (0.325 g, 77%), which was used without further purification in the next step.

$^1$H-NMR (400 MHz, DMSO-$d_6$): δ=6.25 (d, 1H), 6.58 (s, 2H), 7.68 (d, 1H).

HPLC-MS: Rt 3.223 m/z 300.8 (MH$^+$).

Intermediate 2

5,6-diiodopyridin-2-amine

Intermediate 2 was Synthetized Using the Procedure Described for Intermediate 1 Starting from 6-iodopyridin-2-amine $^1$H-NMR (400 MHz, DMSO-$d_6$): δ=6.26 (d, 1H), 6.49(s, 1H), 7.54(d, 1H).

HPLC-MS: Rt 3.373 m/z 346.8(MH$^+$).

Intermediate 3

6-(pyrimidin-5-yl) pyridin-2-amine

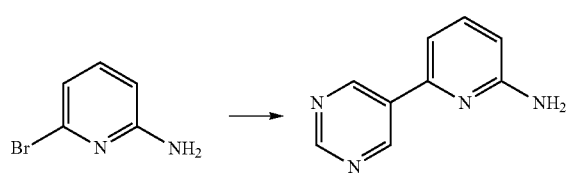 [SMILES: Nc1cccc(Br)n1 ; Nc1cccc(-c2cncnc2)n1]

A mixture of 6-bromopyridin-2-amine (0.5 g, 2.89 mmol) and (pyrimidin-5-yl) boronic acid pinacolester (0.80 g, 3.9 mmol), [1,1'-Bis(diphenylphosphino)ferrocene]dichloropalladium(II), complex with dichloromethane (0.047 g, 0.057 mmol) and 2M aqueous cesium carbonate solution (3 mL) in 1,4-dioxane (15 mL) was heated to 110° C. and left to stir 20 hours. The mixture was cooled, filtered over celite to remove remaining palladium and then partitioned between ethyl acetate and 1M aqueous sodium hydroxide solution. The organic phase was further partitioned with sodium bicarbonate and brine. The final organic layer was dried (MgSO$_4$) and evaporated under reduced pressure. The residue precipitates as a black solid using pentane (0.671 g, 65%), which was used without further purification in the next step.

$^1$H-NMR (400 MHz, DMSO-$d_6$): δ=6.20 (s, 2H), 6.51 (d, 1H), 7.20 (d, 1H), 7.52 (t, 1H), 9.18 (s, 1H), 9.31 (s, 2H).

HPLC-MS: Rt 1.718 m/z 173.1 (MH$^+$).

The following intermediates 4 to 11 were synthesized from 6-bromopyridin-2-amine using the procedure described for Intermediate 3 and the corresponding boronic acid or boronate derivative.

Intermediate 4

6-(pyridin-3-yl)pyridin-2-amine $^1$H-NMR (400 MHz, DMSO-$d_6$): δ=6.09 (s, 2H), 6.47 (d, 1H), 7.12 (d, 1H), 7.45 (t, 1H), 7.49 (t, 1H), 8.29 (d, 1H), 8.56 (d, 1H), 9.15 (s, 1H).

HPLC-MS: Rt 2.229 m/z 172.1 (MH$^+$).

Intermediate 5

6-(5-fluoropyridin-3-yl)pyridin-2-amine $^1$H-NMR (400 MHz, DMSO-$d_6$): δ=6.17 (s, 2H), 6.50 (d, 1H), 7.22 (d, 1H), 7.51 (t, 1H), 8.19 (dd, 1H), 8.57 (d, 1H), 9.06 (s, 1H).

HPLC-MS: Rt 2.420 m/z 190.1 (MH$^+$).

Intermediate 6

6-(5-methoxypyridin-3-yl)pyridin-2-amine $^1$H-NMR (400 MHz, DMSO-$d_6$): δ=3.89 (s, 3H), 6.11 (s, 2H), 6.47 (d, 1H), 7.15 (d, 1H), 7.48 (t, 1H), 7.84 (dd, 1H), 8.28 (d, 1H), 8.75 (d, 1H).

HPLC-MS: Rt 2.406 m/z 202.1 (H$^+$).

Intermediate 7

6-[5-(trifluoromethyl)pyridin-3-yl]pyridin-2-amine $^1$H-NMR (400 MHz, DMSO-$d_6$): δ=6.25 (s, 2H), 6.53 (d, 1H), 7.32 (d, 1H), 7.53 (t, 1H), 8.67 (s, 1H), 8.96 (d, 1H), 9.46 (d, 1H).

HPLC-MS: Rt 3.213 m/z 240.1 (MH$^+$).

Intermediate 8

6-(pyridin-4-yl)pyridin-2-amine $^1$H-NMR (400 MHz, DMSO-$d_6$): δ=6.15 (s, 2H), 6.53 (d, 1H), 7.20 (d, 1H), 7.51 (t, 1H), 7.92 (d, 2H), 8.62 (d, 2H).

HPLC-MS: Rt 2.146 m/z 172.1 (MH$^+$).

Intermediate 9

6-(5-chloropyridin-3-yl)pyridin-2-amine $^1$H-NMR (400 MHz, DMSO-$d_6$): δ=6.17 (s, 2H), 6.50 (d, 1H), 7.21 (d, 1H), 7.50 (t, 1H), 8.42 (t, 1H), 8.61 (d, 1H), 9.12 (d, 1H).

HPLC-MS: Rt 2.830 m/z 206.0 (MH$^+$).

Intermediate 10

6-(6-methoxypyridin-3-yl)pyridin-2-amine $^1$H-NMR (400 MHz, DMSO-d$_6$): δ=3.89 (s, 3H), 6.01 (s, 2H), 6.41 (d, 1H), 6.88 (d, 1H), 7.03 (d, 1H), 7.45 (t, 1H), 8.25 (dd, 1H), 8.74 (s, 1H).
HPLC-MS: Rt 2.779 m/z 202.1 (MH$^+$).

Intermediate 11

6-(3-fluoropyridin-4-yl)pyridin-2-amine $^1$H-NMR (400 MHz, DMSO-d$_6$): δ=6.20 (s, 2H), 6.56 (d, 1H), 7.05 (dd, 1H), 7.53 (t, 1H), 7.91 (dd, 1H), 8.51 (d, 1H), 8.63 (d, 1H).
HPLC-MS: Rt 2.380 m/z 190.1 (MH$^+$).

Intermediate 12

5-iodo-6-(pyrimidin-5-yl)pyridin-2-amine

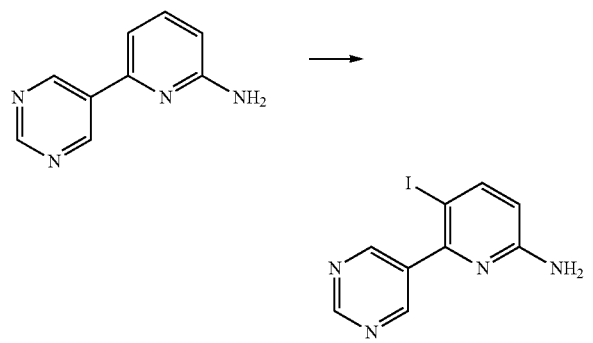

N-iodosuccinimide (0.796 g, 3.54 mmol) was added to a solution of 6-(pyrimidin-5-yl) pyridin-2-amine (0.67 g, 3.9 mmol) in glacial acetic acid (2 mL). The mixture was stirred at room temperature 4 hours. The acid was evaporated under reduced pressure and the residue basified with aqueous sodium bicarbonate saturated solution. The aqueous phase was removed and a brown solid was obtained by washing with water which was purified by column (97:3 Dichloromethane: methanol). The purified compound was a beige solid (0.531 g, 47.5%).

$^1$H-NMR (400 MHz, DMSO-d$_6$): δ=6.36 (d, 1H), 6.43 (s, 2H), 7.86 (d, 1H), 8.94 (s, 2H), 9.21 (s, 1H).
HPLC-MS: Rt 2.441 m/z 299.0 (MH$^+$).

The following intermediates 13 to 20 were synthetized using the procedure described for Intermediate 12, but starting from the corresponding 6-substituted pyridin2-amine.

Intermediate 13

5-iodo-6-(pyridin-3-yl)pyridin-2-amine $^1$H-NMR (400 MHz, DMSO-d$_6$): δ=6.30 (d, 1H), 6.32 (s, 2H), 7.45 (t, 1H), 7.83 (d, 1H), 7.87 (d, 1H), 8.57 (d, 1H), 8.66 (s, 1H).
HPLC-MS: Rt 2.817 m/z 297.9 (MH$^+$).

Intermediate 14

6-(5-fluoropyridin-3-yl)-5-iodopyridin-2-amine $^1$H-NMR (400 MHz, DMSO-d$_6$): δ =6.33 (d, 1H), 6.38 (s, 2H), 7.82 (dd, 1H), 7.84 (d, 1H), 8.55 (s, 1H), 8.60 (d, 1H).
HPLC-MS: Rt 3.086 m/z 315.9 (MH$^+$).

Intermediate 15

5-iodo-6-(methoxypyridin-3-yl)pyridin-2-amine $^1$H-NMR (400 MHz, DMSO-d$_6$): δ=3.86 (s, 3H), 6.31 (d, 1H), 6.33 (s, 2H), 7.42 (dd, 1H), 7.83 (d, 1H), 8.25 (d, 1H), 8.29 (d, 1H).
HPLC-MS: Rt 2.990 m/z 327.9 (MH$^+$).

Intermediate 16

6-[5-(trifluoromethyl)pyridin-3-yl]-5-iodopyridin-2-amine $^1$H-NMR (400 MHz, DMSO-d$_6$): δ=6.35 (d, 1H), 6.43 (s, 2H), 7.86 (d, 1H), 8.28 (s, 1H), 9.00 (dd, 1H), 9.02 (d, 1H).
HPLC-MS: Rt 3.795 m/z 365.9 (MH$^+$).

Intermediate 17

5-iodo-6-(pyridin-4-yl)pyridin-2-amine $^1$H-NMR (400 MHz, DMSO-d$_6$): δ=6.33 (d, 1H), 6.38 (s, 2H), 7.48 (d, 2H), 7.84 (d, 1H), 8.65 (d, 2H).
HPLC-MS: Rt 2.744 m/z 298.0 (MH$^+$).

Intermediate 18

6-(5-chloropyridin-3-yl)-5-iodopyridin-2-amine $^1$H-NMR (400 MHz, DMSO-d$_6$): δ=6.33 (d, 1H), 6.37 (s, 2H), 7.84 (d, 1H), 8.01 (t, 1H), 8.65 (t, 2H).
HPLC-MS: Rt 3.426 m/z 331.9 (MH$^+$).

Intermediate 19

6-(6-methoxypyridin-3-yl)-5-iodopyridin-2-amine $^1$H-NMR (400 MHz, DMSO-d$_6$): δ=3.90 (s, 3H), 6.28 (d, 3H), 6.86 (d, 1H), 7.81 (dd, 2H), 8.30 (d, 1H).
HPLC-MS: Rt 3.401 m/z 328.0 (MH$^+$).

Intermediate 20

6-(3-fluoropyridin-4-yl)-5-iodopyridin-2-amine $^1$H-NMR (400 MHz, DMSO-d$_6$): δ=6.37 (d, 1H), 6.40 (s, 2H), 7.40 (dd, 1H), 7.82 (d, 1H), 8.52 (dd, 1H), 8.67 (d, 1H).
HPLC-MS: Rt 2.937 m/z 315.9 (MH$^+$).

EXAMPLES

Example 1

5-(pyridin-4-yl)-6-(pyrimidin-5-yl)pyridin-2-amine

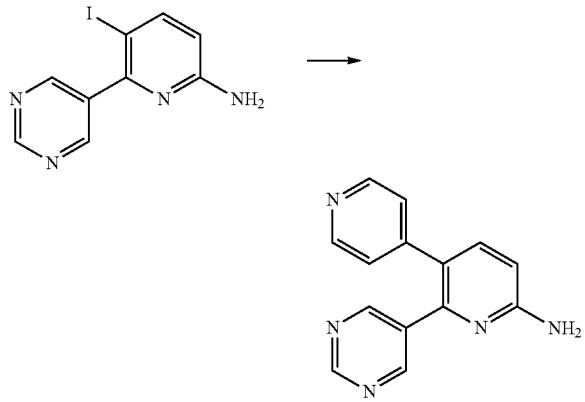

A mixture of 5-iodo-6-(pyrimidin-5-yl)pyridin-2-amine (0.53 g, 1.77 mmol) and (pyridin-4-yl) boronic acid pinacolester (0.91 g, 4.42 mmoles), [1,1'Bis(diphenylphosphino) ferrocene] dichloropalladium (II), complex with dichloromethane (0.087 g, 0.107 mmoles) and 2M aqueous cesium carbonate solution (3.6 mL) in 1,4-dioxane (14.3 mL) was heated to 110° C. and left to stir 20 hours. The mixture was cooled and then partitioned between ethyl acetate and 1M aqueous sodium hydroxide solution. The organic phase was partitioned to with sodium bicarbonate and brine. The final organic layer was dried (MgSO4) and evaporated. The residue precipitates as a light pink fine solid washed with cooled diethyl ether and was dried (0.286 g, 54.8%).

$^1$H-NMR (400 MHz, DMSO-$d_6$): δ=6.52 (s, 2H), 6.64 (d, 1H), 7.13 (d, 2H), 7.58 (d, 1H), 8.44 (d, 2H), 8.61 (s, 2H), 9.09 (s, 1H).

HPLC-MS: Rt 1.886 m/z 250.1 (MH$^+$).

Example 2

5-(3-fluoropyridin-4-yl)-6-(pyrimidin-5-yl)pyridin-2-amine

The product was synthesized from 6-(pyrimidin-5-yl) pyridin-2-amine and 3-fluoropyridin-4-boronic acid, following the procedure described for Example 1.

$^1$H-NMR (400 MHz, DMSO-$d_6$): δ=6.61 (s, 2H), 6.65 (d, 1H), 7.38 (dd, 1H), 7.57 (d, 1H), 8.39 (d, 1H), 8.43 (d, 1H), 8.62 (s, 2H), 9.10 (s, 1H).

HPLC-MS: Rt 2.082 m/z 268.0 (MH$^+$).

Example 3

6-(pyridin-3-yl)-5-(pyridin-4-yl)pyridin-2-amine

The product was synthesized from 6-(pyridin-3-yl)pyridin-2-amine and pyridin-4-boronic acid, following the procedure described for Example 1.

$^1$H-NMR (400 MHz, DMSO-$d_6$): δ=6.42 (s, 2H), 6.59 (d, 1H), 7.06 (d, 2H), 7.30 (dd, 1H), 7.55 (d, 1H), 7.63 (d, 1H), 8.37 (d, 1H), 8.39 (d, 2H), 8.46 (d, 1H).

HPLC-MS: Rt 2.804 m/z 249.1 (MH$^+$).

Example 4

5-(3-fluoropyridin-4-yl)-6-(pyridin-3-yl)pyridin-2-amine

The product was synthesized from 6-(pyridin-3-yl)pyridin-2-amine and 3-fluoropyridin-4-boronic acid, following the procedure described for Example 1.

$^1$H-NMR (400 MHz, DMSO-$d_6$): δ=6.50 (s, 2H), 6.60 (d, 1H), 7.30 (m, 2H), 7.52 (d, 1H), 7.61 (d, 1H), 8.35 (d, 1H), 8.37 (m, 2H), 8.45 (d, 1H).

HPLC-MS: Rt 2.357 m/z 267.1 (MH$^+$).

Example 5

6-(pyridin-3-yl)-5-(pyrimidin-5-yl)pyridin-2-amine

The product was synthesized from 6-(pyridin-3-yl)pyridin-2-amine and pyrimidin-5-boronic, following the procedure described for Example 1.

$^1$H-NMR (400 MHz, DMSO-$d_6$): δ=6.45 (s, 2H), 6.62 (d, 1H), 7.31 (dd, 1H), 7.61 (d, 1H), 7.64 (dd, 1H), 8.40 (d, 1H), 8.47 (dd, 1H), 8.50 (s, 2H), 8.99 (s, 1H).

HPLC-MS: Rt 1.753 m/z 250.1 (MH$^+$).

Example 6

6-(5-fluoropyridin-3-yl)-5-(3-fluoropyridin-4-yl) pyridin-2-amine

The product was synthesized from 6-(5-fluoropyridin-3-yl)pyridin-2-amine and 3-fluoropyridin-4-boronic acid, following the procedure described for Example 1.

$^1$H-NMR (400 MHz, DMSO-$d_6$): δ=6.57 (s, 2H), 6.64 (d, 1H), 7.36 (dd, 1H), 7.56 (d, 1H), 7.59 (dd, 1H), 8.19 (t, 1H), 8.39 (d, 1H), 8.42 (d, 1H), 8.50 (d, 1H).

HPLC-MS: Rt 2.534 m/z 285.0 (MH$^+$).

Example 7

5-(3-fluoropyridin-4-yl)-6-(5-methoxypyridin-3-yl) pyridin-2-amine

The product was synthesized from 6-(5-methoxypyridin-3-yl)pyridin-2-amine and 3-fluoropyridin-4-boronic acid, following the procedure described for Example 1.

$^1$H-NMR (400 MHz, DMSO-$d_6$): δ=3.69 (s, 3H), 6.52 (s, 2H), 6.60 (d, 1H), 7.20 (dd, 1H), 7.32 (dd, 1H), 7.52 (d, 1H), 7.94 (d, 1H), 8.18 (d, 1H), 8.36 (d, 1H), 8.41 (d, 1H).

HPLC-MS: Rt 2.499 m/z 297.1 (MH$^+$).

Example 8

6-[5-(trifluoromethyl)pyridin-3-yl]-5-(3-fluoropyridin-4-yl)pyridin-2-amine

The product was synthesized from 6-(5-(trifluoromethyl) pyridin-3-yl)pyridin-2-amine and 3-fluoropyridin-4-boronic acid, following the procedure described for Example 1.

$^1$H-NMR (400 MHz, DMSO-$d_6$): δ=6.64 (s, 2H), 6.66 (d, 1H), 7.39 (dd, 1H), 7.58 (d, 1H), 8.01 (t, 1H), 8.40 (d, 1H), 8.42 (d, 1H), 8.63 (d, 1H), 8.89 (d, 1H).

HPLC-MS: Rt 3.134 m/z 335.0 (MH$^+$).

Example 9

6-(5-chloropyridin-3-yl)-5-(3-fluoropyridin-4-yl)pyridin-2-amine

The product was synthesized from 6-(5-chloropyridin-3-yl)pyridin-2-amine and 3-fluoropyridin-4-boronic acid, following the procedure described for Example 1.

$^1$H-NMR (400 MHz, DMSO-d$_6$): δ=6.57 (s, 2H), 6.63 (d, 1H), 7.36 (dd, 1H), 7.55 (d, 1H), 7.80 (t, 1H), 8.24 (t, 1H), 8.39 (dd, 1H), 8.43 (d, 1H), 8.54 (d, 1H).
HPLC-MS: Rt 2.860 m/z 301.0 (MH$^+$).

Example 10: 5-(3-fluoropyridin-4-yl)-6-(6-methoxypyridin-3-yl)pyridin-2-amine The product was synthesized from 6-(6-methoxypyridin-3-yl)pyridin-2-amine and 3-fluoropyridin-4-boronic acid, following the procedure described for Example 1.

$^1$H-NMR (400 MHz, DMSO-d$_6$): δ=3.81 (s, 3H), 6.48 (s, 2H), 6.58 (d, 1H), 6.74 (d, 1H), 7.40 (s, 1H), 7.50 (d, 1H), 7.59 (d, 1H), 7.95 (s, 1H), 8.41 (d, 2H).
HPLC-MS: Rt 2.741 m/z 297.1 (MH$^+$).

Example 11

5-(3-fluoropyridin-4-yl)-6-(pyridin-4-yl)pyridin-2-amine

The product was synthesized from 6-(pyridin-4-yl)pyridin-2-amine and 3-fluoropyridin-4-boronic acid, following the procedure described for Example 1.

$^1$H-NMR (400 MHz, DMSO-d$_6$): δ=6.54 (s, 2H), 6.63 (d, 1H), 7.19 (d, 2H), 7.32 (dd, 1H), 7.53 (d, 1H), 8.37 (dd, 1H), 8.40 (d, 1H), 8.46 (d, 2H).

Example 12

5,6-bis(3-fluoropyridin-4-yl)pyridin-2-amine

The product was synthesized from 6-(3-fluoropyridin-4-yl)pyridin-2-amine and 3-fluoropyridin-4-boronic acid, following the procedure described for Example 1.

$^1$H-NMR (400 MHz, DMSO-d$_6$): δ=6.59 (s, 2H), 6.67 (d, 1H), 7.19 (dd, 1H), 7.41 (dd, 1H), 7.58 (d, 1H), 8.30 (dd, 1H), 8.41 (dd, 1H), 8.43 (d, 2H).
HPLC-MS: Rt 2.408 m/z 285.0 (MH$^+$).

Example 13

5-(3-chloropyridin-4-yl)-6-(pyridin-3-yl)pyridin-2-amine

The product was synthesized from 6-(pyridin-3-yl)pyridin-2-amine and 3-chloropyridin-4-boronic acid, following the procedure described for Example 1.

$^1$H-NMR (400 MHz, DMSO-d$_6$): δ=6.46 (s, 2H), 6.59 (d, 1H), 7.26 (dd, 1H), 7.32 (d, 1H), 7.43 (d, 1H), 7.57 (m, 1H), 8.35 (d, 1H), 8.42 (dd, 2H), 8.54 (s, 1H).
HPLC-MS: Rt 2.560 m/z 283.0 (MH$^+$).

Example 14

5-(3-chloropyridin-4-yl)-6-(pyridin-4-yl)pyridin-2-amine

The product was synthesized from 6-(pyridin-4-yl)pyridin-2-amine and 3-chloropyridin-4-boronic acid, following the procedure described for Example 1.

$^1$H-NMR (400 MHz, DMSO-d$_6$): δ=6.48 (s, 2H), 6.61 (d, 1H), 7.15 (dd, 2H), 7.29 (d, 1H), 7.43 (d, 1H), 8.43 (d, 2H), 8.57 (s, 1H).
HPLC-MS: Rt 2.563 m/z 283.0 (MH$^+$).

Example 15

5-(2-chloro-6-methylpyridin-4-yl)-6-(pyridin-3-yl)pyridin-2-amine

The product was synthesized from 6-(pyridin-3-yl)pyridin-2-amine and 2-chloro-6-methylpyridin-4-boronic acid, following the procedure described for Example 1.

$^1$H-NMR (400 MHz, DMSO-d$_6$): δ=2.32 (s, 3H), 6.49 (s, 2H), 6.57 (d, 1H), 6.91-6.89 (m, 1H), 6.99-6.96 (m, 1H), 7.36-7.30 (m, 1H), 7.56 (d, 1H), 7.66-7.61 (m, 1H), 8.40-8.38 (m, 1H), 8.49 (dd, 1H).
HPLC-MS: Rt 3.110 m/z 297.1 (MH$^+$).

Example 16

5-(2-methoxypyridin-4-yl)-6-(pyridin-3-yl)pyridin-2-amine

The product was synthesized from 6-(pyridin-3-yl)pyridin-2-amine and 2-methoxypyridin-4-boronic acid, following the procedure described for Example 1.

$^1$H-NMR (400 MHz, DMSO-d$_6$): δ=3.79 (s, 3H), 6.40 (s, 2H), 6.61-6.53 (m, 3H), 7.32 (ddd, 1H), 7.53 (dd, 1H), 7.65 (dq, 1H), 7.96 (dd, 1H), 8.42-8.33 (m, 1H), 8.46 (dd, 1H).

Example 17

3-chloro-5-(pyridin-4-yl)-6-(pyrimidin-5-yl)pyridin-2-amine

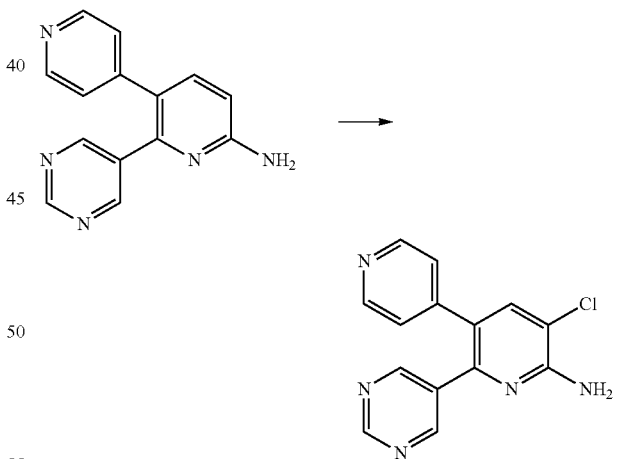

N-chlorosuccinimide (0.0613 g, 0.46 mmol) was added to a solution of 6-(pyridin-4-yl)-5-(pyrimidin-5-yl)pyridin-2-amine (0.135 g, 0.46 mmol) in N,N-dimethylformamide (0.8 mL). The mixture was stirred at room temperature 4 hours, then it was treated with a saturated aqueous sodium chloride solution (10 mL), filtered and the solid washed with water. The resulted solid was dried in vacuum to give the tittle compound 0.1 g as a 65.3%.

$^1$H-NMR (400 MHz, DMSO-d$_6$): δ=6.88 (s, 2H), 7.18 (d, 2H), 7.84 (s, 1H), 8.47 (d, 2H), 8.62 (s, 2H), 9.10 (s, 1H).
HPLC-MS: Rt 2.416 m/z 284.0 (MH$^+$).

Compounds of the Examples 18 to 42 were synthesized using the procedure described for example 17, from 5,6-disubstituted pyridine-2-amine and the corresponding N-halosuccinimide.

Example 18

3-bromo-5-(pyridin-4-yl)-6-(pyrimidin-5-yl)pyridin-2-amine $^1$H-NMR (400 MHz, DMSO-$d_6$): δ=6.82 (s, 2H), 7.19 (d, 2H), 7.96 (s, 1H), 8.47 (d, 2H), 8.62 10 (s, 2H), 9.11 (s, 1H).
HPLC-MS: Rt 2.536 m/z 328.0 (MH$^+$).

Example 19

3-chloro-5-(3-fluoropyridin-4-yl)-6-(pyrimidin-5-yl)pyridin-2-amine $^1$H-NMR (400 MHz, DMSO-$d_6$): δ=6.98 (s, 2H), 7.44 (dd, 1H), 7.87 (s, 1H), 8.42 (d, 1H), 8.46 (d, 1H), 8.64 (s, 2H), 9.12 (s, 1H).
HPLC-MS: Rt 2.676 m/z 302.0 (MH$^+$).

Example 20

3-bromo-5-(3-fluoropyridin-4-yl)-6-(pyrimidin-5-yl)pyridin-2-amine $^1$-H-NMR (400 MHz, DMSO-$d_6$): δ=6.92 (s, 2H), 7.44 (dd, 1H), 7.99 (s, 1H), 8.42 (d, 1H), 8.45 (d, 1H), 8.64 (s, 2H), 9.12 (s, 1H).
HPLC-MS: Rt 2.717 m/z 348.0 (MH$^+$).

Example 21

3-chloro-6-(pyridin-3-yl)-5-(pyridin-4-yl)pyridin-2-amine $^1$H-NMR (400 MHz, DMSO-$d_6$): δ=6.78 (s, 2H), 7.12 (d, 2H), 7.32 (dd, 1H), 7.63 (d, 1H), 7.78 (s, 1H), 8.38 (s, 1H), 8.42 (d, 2H), 8.48 (d, 1H).
HPLC-MS: Rt 2.714 m/z 283.0 (MH$^+$).

Example 22

3-bromo-6-(pyridin-3-yl)-5-(pyridin-4-yl)pyridin-2-amine $^1$H-NMR (400 MHz, DMSO-$d_6$): δ=6.72 (s, 2H), 7.12 (d, 2H), 7.32 (dd, 1H), 7.63 (d, 1H), 7.91 (s, 1H), 8.39 (s, 1H), 8.43 (d, 2H), 8.48 (d, 1H).
HPLC-MS: Rt 2.810 m/z 329.0 (MH$^+$).

Example 23

3-chloro-5-(3-fluoropyridin-4-yl)-6-(pyridin-3-yl)pyridin-2-amine $^1$H-NMR (400 MHz, DMSO-$d_6$): δ=6.89 (s, 2H), 7.31 (dd, 1H), 7.40 (t, 1H), 7.61 (d, 1H), 7.80 (s, 1H), 8.38 (d, 1H), 8.40 (s, 1H), 8.42 (d, 1H), 8.48 (d, 1H).
HPLC-MS: Rt 2.904 m/z 301.0 (MH$^+$).

Example 24

3-bromo-5-(3-fluoropyridin-4-yl)-6-(pyridin-3-yl)pyridin-2-amine $^1$H-NMR (400 MHz, DMSO-$d_6$): δ=6.81 (s, 2H), 7.31 (dd, 1H), 7.40 (t, 1H), 7.61 (d, 1H), 7.92 (s, 1H), 8.38 (d, 1H), 8.41 (d, 1H), 8.42 (d, 1H), 8.48 (d, 1H).
HPLC-MS: Rt 3.055 m/z 345.0 (MH$^+$).

Example 25

3-chloro-6-(pyridin-3-yl)-5-(pyrimidin-5-yl)pyridin-2-amine $^1$H-NMR (400 MHz, DMSO-$d_6$): δ=6.82 (s, 2H), 7.33 (dd, 1H), 7.64 (d, 1H), 7.92 (s, 1H), 8.42 (d, 1H), 8.49 (d, 1H), 8.55 (s, 2H), 9.02 (s, 1H).
HPLC-MS: Rt 2.283 m/z 284.0 (MH$^+$).

Example 26

3-bromo-6-(pyridin-3-yl)-5-(pyrimidin-5-yl)pyridin-2-amine $^1$H-NMR (400 MHz, DMSO-$d_6$): δ=6.74 (s, 2H), 7.32 (dd, 1H), 7.64 (d, 1H), 8.04 (s, 1H). 8,42 (d, 1H), 8.49 (d, 1H), 8.55 (s, 2H), 9.02 (s, 1H).15
HPLC-MS: Rt 2.381 m/z 330.0 (MH$^+$).

Example 27

3-chloro-6-(5-fluoropyridin-3-yl)-5-(3-fluoropyridin-4-yl)pyridin-2-amine $^1$H-NMR (400 MHz, DMSO-$d_6$): δ=6.93 (s, 2H), 7.41 (dd, 1H), 7.59 (d, 1H), 7.83 (s, 1H), 8.20 (s, 1H), 8.41 (d, 1H), 8.45 (s, 1H), 8.52 (d, 1H).
HPLC-MS: Rt 3.121 m/z 319.0 (MH$^+$).

Example 28

3-bromo-6-(5-fluoropyridin-3-yl)-5-(3-fluoropyridin-4-yl)pyridin-2-amine $^1$H-NMR (400 MHz, DMSO-$d_6$): δ=6.87 (s, 2H), 7.42 (dd, 1H), 7.60 (d, 1H), 7.96 (s, 1H), 8.21 (s, 1H), 8.41 (d, 1H), 8.44 (s, 1H), 8.52 (d, 1H).
HPLC-MS: Rt 3.199 m/z 365.0 (MH$^+$).

Example 29

3-chloro-5-(3-fluoropyridin-4-yl)-6-(5-methoxypyridin-3-yl)pyridin-2-amine $^1$H-NMR (400 MHz, DMSO-$d_6$): δ=3.69 (s, 3H), 6.89 (s, 2H), 7.21 (dd, 1H), 7.40 (dd, 1H), 7.81 (s, 1H), 7.96 (s, 1H), 8.21 (d, 1H), 8.40 (d, 1H), 8.44 (s, 1H).
HPLC-MS: Rt 3.037 m/z 331.0 (MH$^+$).

Example 30

3-bromo-5-(3-fluoropyridin-4-yl)-6-(5-methoxypyridin-3-yl)pyridin-2-amine $^1$H-NMR (400 MHz, DMSO-$d_6$): δ=3.69 (s, 3H), 6.82 (s, 2H), 7.23 (dd, 1H), 7.41 (dd, 1H), 7.94 (s, 1H), 7.97 (s, 1H), 8.22 (d, 1H), 8.40 (d, 1H), 8.44 (s, 1H).
HPLC-MS: Rt 3.130 m/z 377.0 (MH$^+$).

Example 31

3-chloro-6-[5-(trifluoromethyl)pyridin-3-yl]-5-(3-fluoropyridin-4-yl)pyridin-2-amine $^1$H-NMR (400 MHz, DMSO-$d_6$): δ=7.01 (s, 2H), 7.46 (dd, 1H), 7.87 (s, 1H), 8.02 (s, 1H), 8.42 (d, 1H), 8.45 (s, 1H), 8.64 (s, 1H), 8.92 (d, 1H).
HPLC-MS: Rt 3.678 m/z 369.0 (MH$^+$).

Example 32

3-bromo-6-[5-(trifluoromethyl)pyridin-3-yl]-5-(3-fluoropyridin-4-yl)pyridin-2-amine $^1$H-NMR (400 MHz, DMSO-$d_6$): δ=6.93 (s, 2H), 7.46 (dd, 1H), 8.00 (s, 1H), 8.03 (s, 1H), 8.42 (d, 1H), 8.45 (s, 1H), 8.64 (d, 1H), 8.92 (d, 1H).
HPLC-MS: Rt 3.769 m/z 413.0 (MH$^+$).

Example 33

3-chloro-6-(5-chloropyridin-3-yl)-5-(3-fluoropyridin-4-yl)pyridin-2-amine $^1$H-NMR (400 MHz, DMSO-$d_6$): δ=6.94 (s, 2H), 7.42 (dd, 1H), 7.81 (t, 1H), 7.84 (s, 1H), 8.25 (d, 1H), 8.42 (d, 1H), 8.46 (d, 1H), 8.56 (d, 1H).

Example 34

3-chloro-5-(3-fluoropyridin-4-yl)-6-(pyridin-4-yl)pyridin-2-amine $^1$H-NMR (400 MHz, DMSO-$d_6$): δ=6.89 (s, 2H), 7.20 (d, 2H), 7.39 (dd, 1H), 7.81 (s, 1H), 8.39 (d, 1H), 8.43 (s, 1H), 8.48 (d, 2H).
HPLC-MS: Rt 2.866 m/z 301.0 (MH$^+$).

Example 35

3-bromo-5-(3-fluoropyridin-4-yl)-6-(pyridin-4-yl)pyridin-2-amine $^1$H-NMR (400 MHz, DMSO-$d_6$): δ=6.85 (s, 2H), 7.20 (d, 2H), 7.40 (t, 1H), 7.94 (s, 1H), 8.40 (d, 1H), 8.43 (s, 1H), 8.48 (d, 2H).
HPLC-MS: Rt 2.963 m/z 347.0 (MH$^+$).

Example 36

3-chloro-5-(3-fluoropyridin-4-yl)-6-(6-methoxypyridin-3-yl)pyridin-2-amine $^1$H-NMR (400 MHz, DMSO-$d_6$): δ=3.81 (s, 3H), 6.75 (d, 1H), 6.80 (s, 2H), 7.40 (dd, 1H), 7.59 (dd, 1H), 7.75 (s, 1H), 7.96 (d, 1H), 8.40 (d, 1H), 8.45 (s, 1H).
HPLC-MS: Rt 3.329 m/z 331.0 (MH$^+$).

Example 37

3-bromo-5-(3-fluoropyridin-4-yl)-6-(6-methoxypyridin-3-yl)pyridin-2-amine $^1$H-NMR (400 MHz, DMSO-$d_6$): δ=3.82 (s, 3H), 6.74 (d, 3H), 7.41 (s, 1H), 7.59 (d, 1H), 7.88 (d, 1H), 7.97 (d, 1H), 8.40 (d, 1H), 8.45 (s, 1H).
HPLC-MS: Rt 3.431 m/z 377.0 (MH$^+$).

Example 38

3-chloro-5,6-bis(3-fluoropyridin-4-yl)pyridin-2-amine $^1$H-NMR (400 MHz, DMSO-$d_6$): δ=6.86 (s, 2H), 7.20 (dd, 1H), 7.42 (dd, 1H), 7.82 (s, 1H), 8.40 (dd, 1H), 8.44 (dd, 1H), 8.45 (d, 2H).

Example 39

3-chloro-5-(3-chloropyridin-4-yl)-6-(pyridin-3-yl)pyridin-2-amine $^1$H-NMR (400 MHz, DMSO-$d_6$): δ=6.90 (s, 2H), 7.35 (dd, 1H), 7.48 (d, 1H), 7.64 (m, 1H), 7.78 (s, 1H), 7.57 (m, 1H), 8.44 (d, 1H), 8.52 (m, 2H), 8.63 (s, 1H).
HPLC-MS: Rt 3.120 m/z 317.0 (MH$^+$).

Example 40

3-chloro-5-(3-chloropyridin-4-yl)-6-(pyridin-4-yl)pyridin-2-amine $^1$H-NMR (400 MHz, DMSO-$d_6$): δ=6.86 (s, 2H), 7.16 (d, 2H), 7.38 (d, 1H), 7.72 (s, 1H), 8.46 (t, 3H), 8.59 (s, 1H).
HPLC-MS: Rt 3.118 m/z 317.0 (MH$^+$).

Example 41

3-chloro-5-(2-chloro-6-methylpyridin-4-yl)-6-(pyridin-3-yl)pyridin-2-amine $^1$H-NMR (400 MHz, DMSO-$d_6$): δ=2.33 (s, 3H), 6.86 (s, 2H), 6.99-6.97 (m, 1H), 7.06-7.03 (m, 1H), 7.38-7.32 (m, 1H), 7.66-7.61 (m, 1H), 7.83 (s, 1H), 8.41 (d, 1H), 8.51 (dd, 1H).

Example 42

3-chloro-5-(2-methoxypyridin-4-yl)-6-(pyridin-3-yl)pyridin-2-amine $^1$H-NMR (400 MHz, DMSO-$d_6$): δ=3.79 (s, 3H), 6.70-6.53 (m, 2H), 6.77 (s, 2H), 7.33 (ddd, 1H), 7.65 (ddd, 1H), 7.76 (s, 1H), 7.98 (dd, 1H), 8.40 (dd, 1H), 8.48 (dd, 1H).

The invention claimed is:
1. A compound of formula (I):

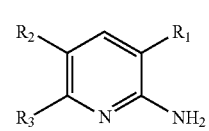

wherein:
R$^1$ represents a halogen atom or hydrogen atom;
R$^2$ represents a six-membered heteroaryl ring optionally substituted by one or more substituents selected from the group consisting of halogen atom, C$_1$-C$_4$ haloalkyl, linear or branched C$_1$-C$_6$ alkyl, C$_3$-C$_{12}$ cycloalkyl, linear or branched C$_1$-C$_6$ alkoxy and C$_3$-C$_{12}$ cycloalkoxy groups;

R³ represents a six-membered heteroaryl ring optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy groups;

or N-oxide of said compounds and pharmaceutically acceptable salt thereof, with the proviso that compound of formula (I) is not:
5-(pyridin-4-yl)-6-(pyridin-4-yl)pyridin-2-amine,
5-(pyridin-3-yl)-6-(pyridin-3-yl)pyridin-2-amine,
5-(pyrazin-2-yl)-6-(pyridin-4-yl)pyridin-2-amine, or
5-(4-methylpyridin-2-yl)-6-(pyridin-4-yl)pyridin-2-amine.

2. A compound according to claim 1 wherein R³ represents a six-membered heteroaryl ring containing one or two nitrogen atoms, optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy.

3. A compound according to claim 2 wherein R³ represents a group selected from pyridyl or pyrimidinyl, optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy.

4. A compound according to claim 3 wherein R³ is selected from 3-pyridyl or 4-pyridyl group, optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy.

5. A compound according to claim 1 wherein R² represents a pyridyl group optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy.

6. A compound according to claim 5 wherein R² represents a 4-pyridyl group optionally substituted by a halogen atom.

7. A compound according to claim 1 wherein R¹ represents a chlorine or bromine atom.

8. A compound according to claim 1 wherein R¹ represents a chlorine or bromine atom, R² represents a 4-pyridyl group optionally substituted by one or two fluorine atoms and R³ represents a group selected from 3-pyridyl or 4-pyridyl, optionally substituted by one or more substituents selected from the group consisting of halogen atom, $C_1$-$C_4$ haloalkyl, linear or branched $C_1$-$C_6$ alkyl, $C_3$-$C_{12}$ cycloalkyl, linear or branched $C_1$-$C_6$ alkoxy and $C_3$-$C_{12}$ cycloalkoxy.

9. A compound according to claim 1 which is one of:
5-(pyridin-4-yl)-6-(pyrimidin-5-yl)pyridin-2-amine,
5-(3-fluoropyridin-4-yl)-6-(pyrimidin-5-yl)pyridin-2-amine,
6-(pyridin-3-yl)-5-(pyridin-4-yl)pyridin-2-amine,
5-(3-fluoropyridin-4-yl)-6-(pyridin-3-yl)pyridin-2-amine,
6-(pyridin-3-yl)-5-(pyrimidin-5-yl)pyridin-2-amine,
6-(5-fluoropyridin-3-yl)-5-(3-fluoropyridin-4-yl)pyridin-2-amine,
5-(3-fluoropyridin-4-yl)-6-(5-methoxypyridin-3-yl)pyridin-2-amine,
6-[5-(trifluoromethyl)pyridin-3-yl]-5-(3-fluoropyridin-4-yl)pyridin-2-amine,
6-(5-chloropyridin-3-yl)-5-(3-fluoropyridin-4-yl)pyridin-2-amine,
5-(3-fluoropyridin-4-yl)-6-(6-methoxypyridin-3-yl)pyridin-2-amine,
5-(3-fluoropyridin-4-yl)-6-(pyridin-4-yl)pyridin-2-amine,
5,6-bis-(3-fluoropyridin-4-yl)pyridin-2-amine,
5-(3-chloropyridin-4-yl)-6-(pyridin-3-yl)pyridin-2-amine,
5-(3-chloropyridin-4-yl)-6-(pyridin-4-yl)pyridin-2-amine,
5-(2-chloro-6-methylpyridin-4-yl)-6-(pyridin-3-yl)pyridin-2-amine,
5-(2-methoxypyridin-4-yl)-6-(pyridin-3-yl)pyridin-2-amine,
3-chloro-5-(pyridin-4-yl)-6-(pyrimidin-5-yl)pyridin-2-amine,
3-bromo-5-(pyridin-4-yl)-6-(pyrimidin-5-yl)pyridin-2-amine,
3-chloro-5-(3-fluoropyridin-4-yl)-6-(pyrimidin-5-yl)pyridin-2-amine,
3-bromo-5-(3-fluoropyridin-4-yl)-6-(pyrimidin-5-yl)pyridin-2-amine,
3-chloro-6-(pyridin-3-yl)-5-(pyridin-4-yl)pyridin-2-amine,
3-bromo-6-(pyridin-3-yl)-5-(pyridin-4-yl)pyridin-2-amine,
3-chloro-5-(3-fluoropyridin-4-yl)-6-(pyridin-3-yl)pyridin-2-amine,
3-bromo-5-(3-fluoropyridin-4-yl)-6-(pyridin-3-yl)pyridin-2-amine,
3-chloro-6-(pyridin-3-yl)-5-(pyrimidin-5-yl)pyridin-2-amine,
3-bromo-6-(pyridin-3-yl)-5-(pyrimidin-5-yl)pyridin-2-amine,
3-chloro-6-(5-fluoropyridin-3-yl)-5-(3-fluoropyridin-4-yl)pyridin-2-amine,
3-bromo-6-(5-fluoropyridin-3-yl)-5-(3-fluoropyridin-4-yl)pyridin-2-amine,
3-chloro-5-(3-fluoropyridin-4-yl)-6-(5-methoxypyridin-3-yl)pyridin-2-amine,
3-bromo-5-(3-fluoropyridin-4-yl)-6-(5-methoxypyridin-3-yl)pyridin-2-amine,
3-chloro-6-[5-(trifluoromethyl)pyridin-3-yl]-5-(3-fluoropyridin-4-yl)pyridin-2-amine,
3-bromo-6-[5-(trifluoromethyl)pyridin-3-yl]-5-(3-fluoropyridin-4-yl)pyridin-2-amine,
3-chloro-6-(5-chloropyridin-3-yl)-5-(3-fluoropyridin-4-yl)pyridin-2-amine,
3-chloro-5-(3-fluoropyridin-4-yl)-6-(pyridin-4-yl)pyridin-2-amine,
3-bromo-5-(3-fluoropyridin-4-yl)-6-(pyridin-4-yl)pyridin-2-amine,
3-chloro-5-(3-fluoropyridin-4-yl)-6-(6-methoxypyridin-3-yl)pyridin-2-amine,
3-bromo-5-(3-fluoropyridin-4-yl)-6-(6-methoxypyridin-3-yl)pyridin-2-amine,
3-chloro-5,6-bis-(3-fluoropyridin-4-yl)pyridin-2-amine,
3-chloro-5-(3-chloropyridin-4-yl)-6-(pyridin-3-yl)pyridin-2-amine,
3-chloro-5-(3-chloropyridin-4-yl)-6-(pyridin-4-yl)pyridin-2-amine,
3-chloro-5-(2-chloro-6-methylpyridin-4-yl)-6-(pyridin-3-yl)pyridin-2-amine,
3-chloro-5-(2-methoxypyridin-4-yl)-6-(pyridin-3-yl)pyridin-2-amine.

10. A pharmaceutical composition comprising a compound as defined in claim 1 and a pharmaceutically acceptable diluent or carrier.

11. A pharmaceutical composition according to claim 10 further comprising a therapeutically effective amount of a therapeutic agent selected from Pirfenidone; Nintedanib; the LPA1 antagonist AM152; dopamine agonists selected from L-Dopa, Ropinirole and Pramipexole; monooxigenase B (MAO-B) enzyme inhibitors selected from Selegiline and Rasagiline; and acetylcholinesterase enzyme inhibitors selected from Galantamine, Rivastigmine, Donepezil and Tacrine.

12. A method for the treatment of disease or pathological condition selected from the group consisting of asthma, chronic obstructive pulmonary disease, idiopathic pulmonary fibrosis diabetes, and cancer comprising administering to a subject in need thereof an effective amount of a compound according to claim 1.

13. A combination product comprising a compound according to claim 1 and a therapeutic agent used for the treatment of a disease selected from the group consisting of asthma, chronic obstructive pulmonary disease, idiopathic pulmonary fibrosis, diabetes, senile dementia, Alzheimer's disease, Parkinson's disease and cancer.

14. A combination product according to claim 13 wherein the therapeutic agent is selected from Pirfenidone, Nintedanib, the LPA1 antagonist AM152, dopamine agonists selected from L-Dopa, Ropinirole and Pramipexole; Monooxigenase B (MAO-B) enzyme inhibitors selected from Selegiline and Rasagiline; and acetylcholinesterase enzyme inhibitors selected from Galantamine, Rivastigmine, Donepezil and Tacrine.

* * * * *